US008447407B2

(12) United States Patent
Talathi et al.

(10) Patent No.: US 8,447,407 B2
(45) Date of Patent: May 21, 2013

(54) METHOD AND SYSTEM FOR DETECTING EPILEPTOGENESIS

(75) Inventors: Sachin S. Talathi, Gainesville, FL (US);
Dong-Uk Hwang, Daejeon (KR);
William L. Ditto, Scottsdale, AZ (US);
Paul R. Carney, Gainesville, FL (US);
Mark Spano, Scottsdale, AZ (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 297 days.

(21) Appl. No.: 12/917,321

(22) Filed: Nov. 1, 2010

(65) Prior Publication Data

US 2011/0130797 A1  Jun. 2, 2011

Related U.S. Application Data

(63) Continuation-in-part of application No. PCT/US2009/042452, filed on Apr. 30, 2009.

(60) Provisional application No. 61/049,046, filed on Apr. 30, 2008.

(51) Int. Cl.
*A61N 1/3605* (2006.01)

(52) U.S. Cl.
USPC ............................. 607/45; 600/544; 600/545

(58) Field of Classification Search
USPC ........................................... 607/45, 544, 545
See application file for complete search history.

(56) References Cited

U.S. PATENT DOCUMENTS

| | | |
|---|---|---|
| 4,735,208 A | 4/1988 | Wyler et al. |
| 5,349,962 A | 9/1994 | Lockard et al. |
| 6,117,066 A | 9/2000 | Abrams et al. |
| 6,529,774 B1 | 3/2003 | Greene |
| 6,549,804 B1 | 4/2003 | Osorio et al. |

(Continued)

FOREIGN PATENT DOCUMENTS

WO    2009/135092    11/2009

OTHER PUBLICATIONS

International Search Report published Feb. 25, 2010 for PCT/US09/042452 filed Apr. 30, 2009.

(Continued)

*Primary Examiner* — Christopher D Koharski
*Assistant Examiner* — Michael Carey
(74) *Attorney, Agent, or Firm* — Fleit Gibbons Gutman Bongini & Bianco, PL; Paul D. Bianco; Gary S. Winer

(57) ABSTRACT

Neuronal excitation and inhibition of the brain is tracked in the hippocampal CA1 network during a latent period, wherein biomarkers are observed which include a sustained increase in the firing rate of the excitatory postsynaptic field activity, paired with a subsequent decrease in the firing rate of the inhibitory postsynaptic field activity; the mean amplitude profiles of both fEPSP and fEPSP field potential activity during the latent period have characteristic shapes; both excitatory and inhibitory CA1 field activity firing rates are observed to follow a circadian rhythm that drifts during epileptogenesis; the circadian rhythms described are in-phase in controls and anti-phase during epileptogenesis; and the fEPSP rate drifts from a circadian rhythm to a greater extent than the fEPSP rate. An additional biomarker is a change in a circadian rhythm of core body temperature. Therapeutic measures can include thermal, chemical, or electrical modulation, in an open or closed loop process.

24 Claims, 10 Drawing Sheets

U.S. PATENT DOCUMENTS

| | | |
|---|---|---|
| 6,978,183 B2 | 12/2005 | Rothman |
| 7,120,486 B2 | 10/2006 | Leuthardt et al. |
| 7,209,787 B2 * | 4/2007 | DiLorenzo ............... 607/45 |
| 2005/0021103 A1 | 1/2005 | DiLorenzo |
| 2005/0131311 A1 | 6/2005 | Leuthardt et al. |
| 2005/0203366 A1 | 9/2005 | Donoghue et al. |
| 2005/0240242 A1 * | 10/2005 | DiLorenzo ............... 607/45 |
| 2005/0273890 A1 | 12/2005 | Flaherty et al. |
| 2005/0283203 A1 | 12/2005 | Flaherty et al. |
| 2006/0058627 A1 | 3/2006 | Flaherty et al. |
| 2006/0142802 A1 * | 6/2006 | Armstrong ............... 607/2 |
| 2006/0217782 A1 * | 9/2006 | Boveja et al. ............ 607/45 |
| 2007/0046486 A1 | 3/2007 | Donoghue et al. |
| 2007/0067003 A1 * | 3/2007 | Sanchez et al. ........... 607/45 |
| 2008/0045853 A1 | 2/2008 | Gluckman et al. |

OTHER PUBLICATIONS

Written Opinion completed Nov. 20, 2009 for PCT/US09/042452 filed Apr. 30, 2009.

International Preliminary Report on Patentability issued Nov. 2, 2010 for PCT/US09/042452 filed Apr. 30, 2009.

Talathi et al, Circadian control of neural excitability in an animal model of temporal lobe epilepsy, Neuroscience Letters 455 (2009) 145-149.

Fisher, et al, Effects of phase on homeostatic spike rates, Biological Cybernetics, published online Mar. 17, 2010.

* cited by examiner

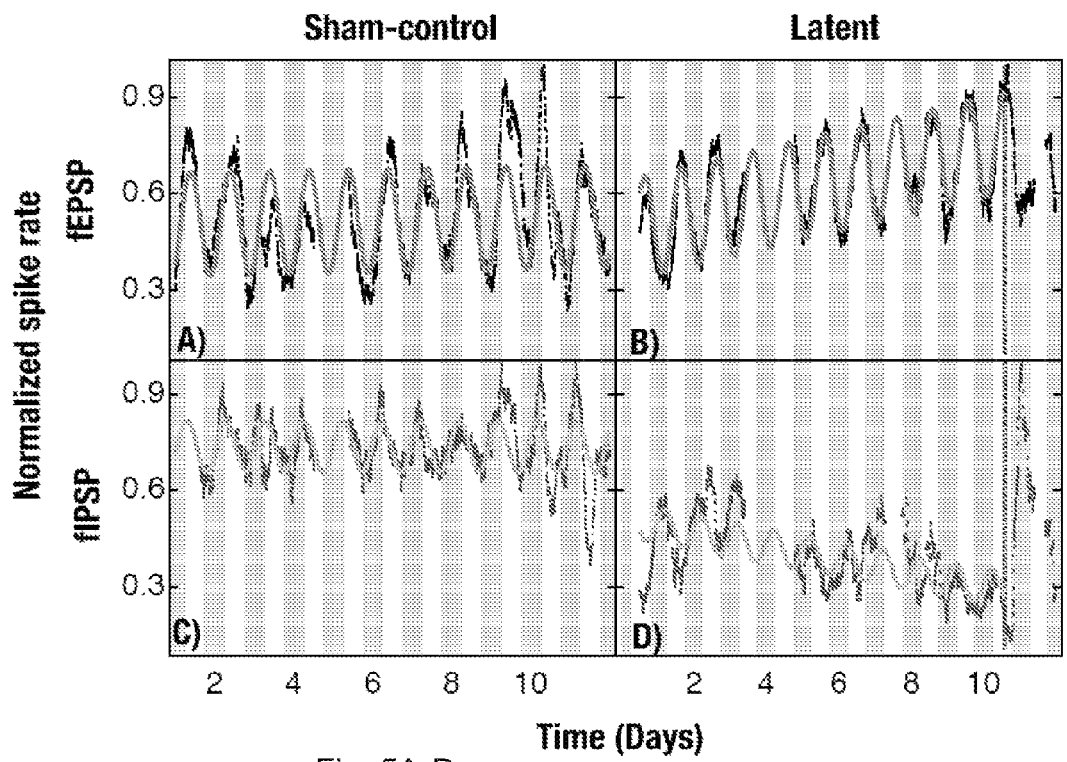
Fig. 5A-D
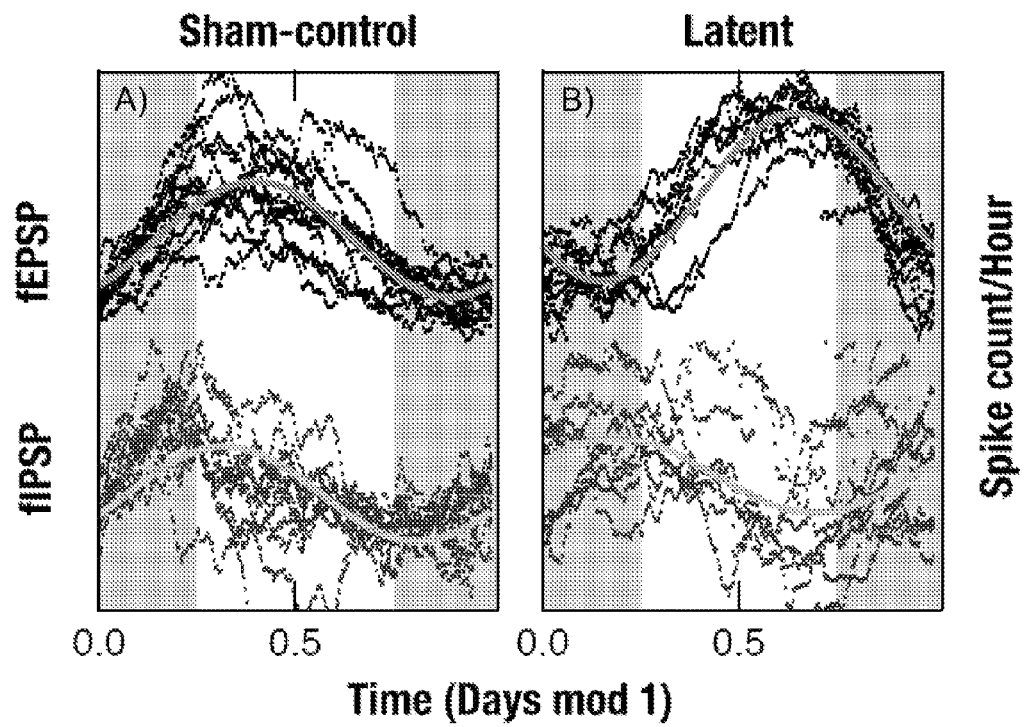
Fig. 6A-B

Fig. 7A-B
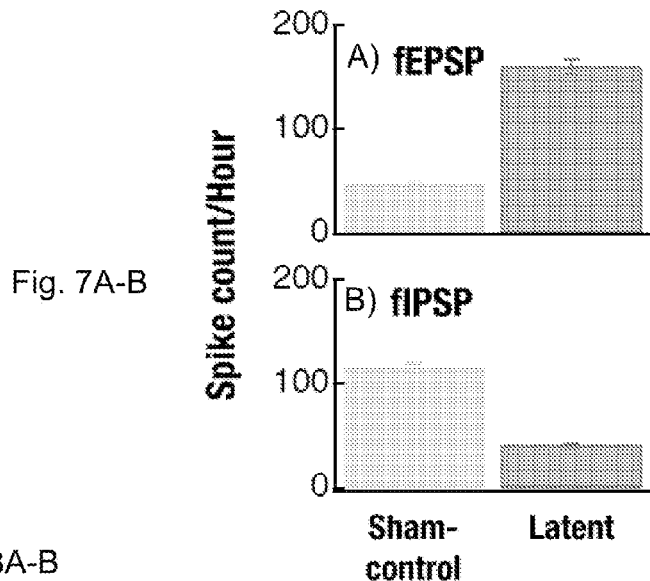
Fig. 8A-B
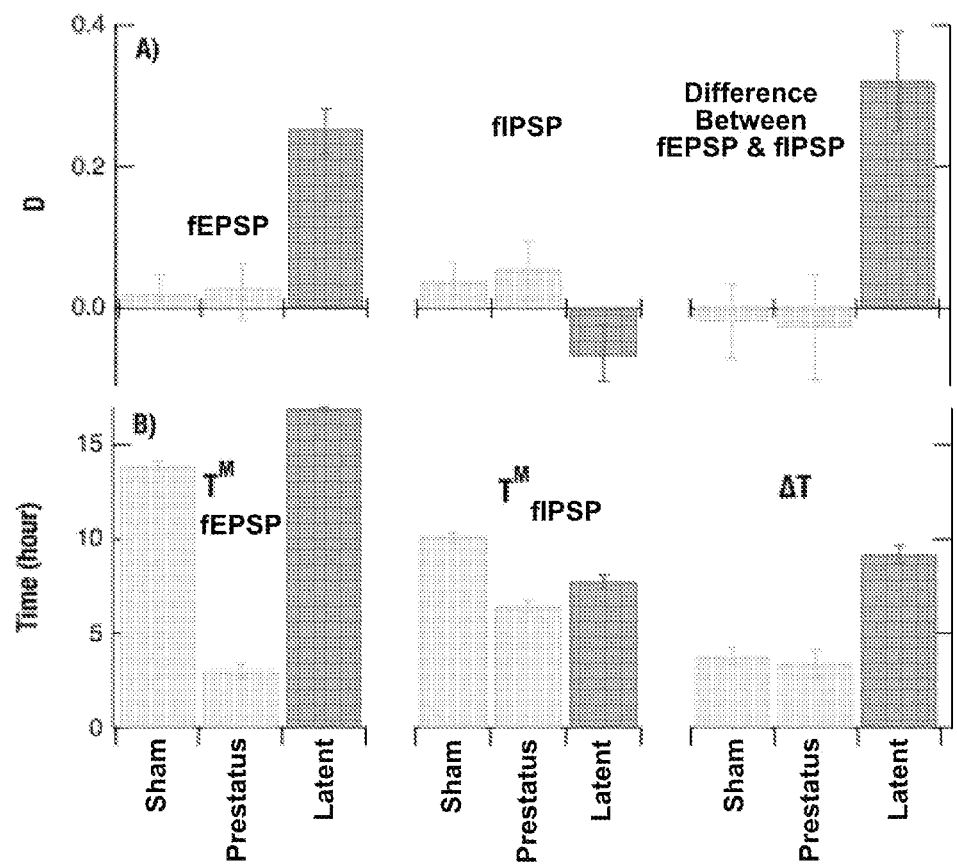

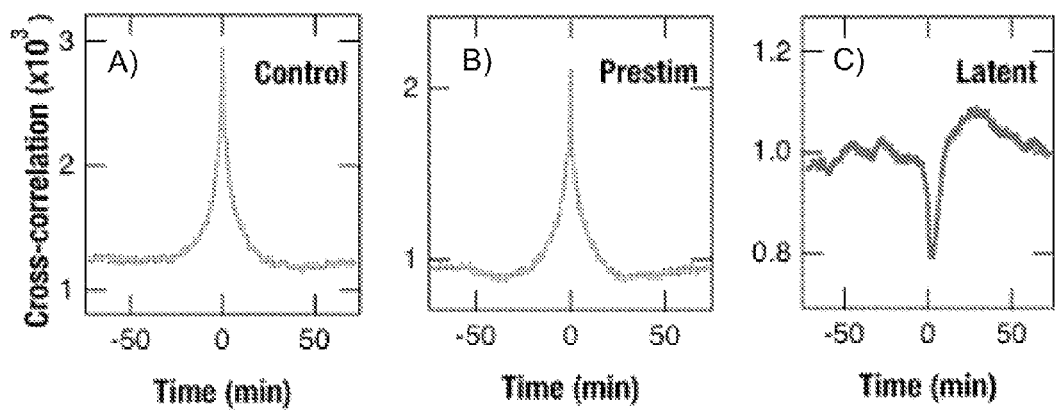
Fig. 9A-C
Fig. 10A-B
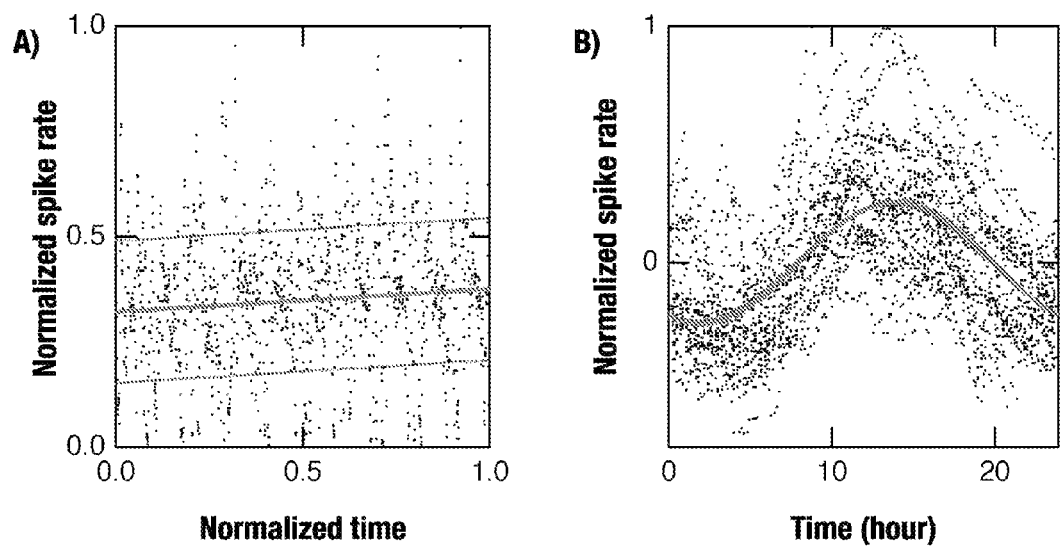

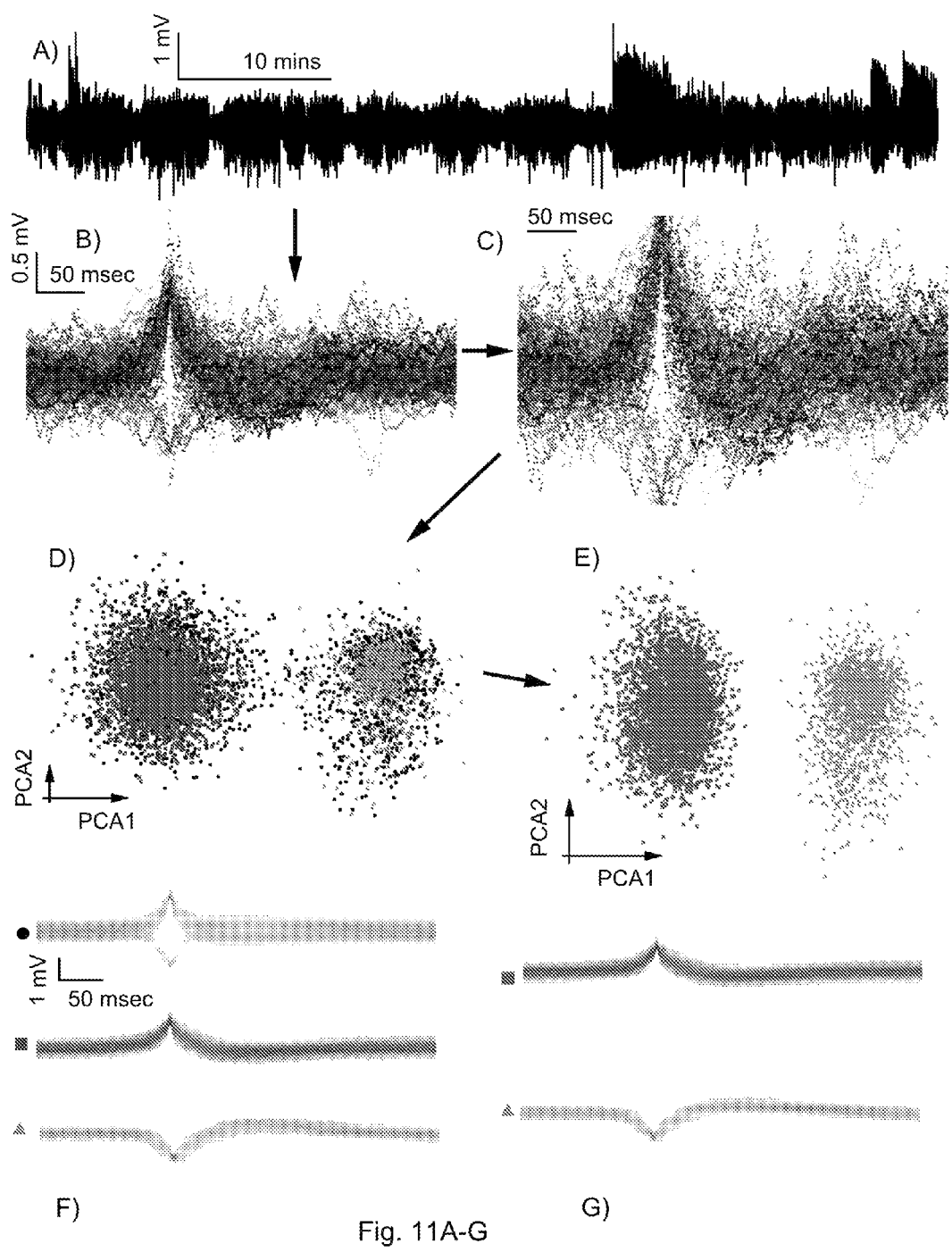
Fig. 11A-G

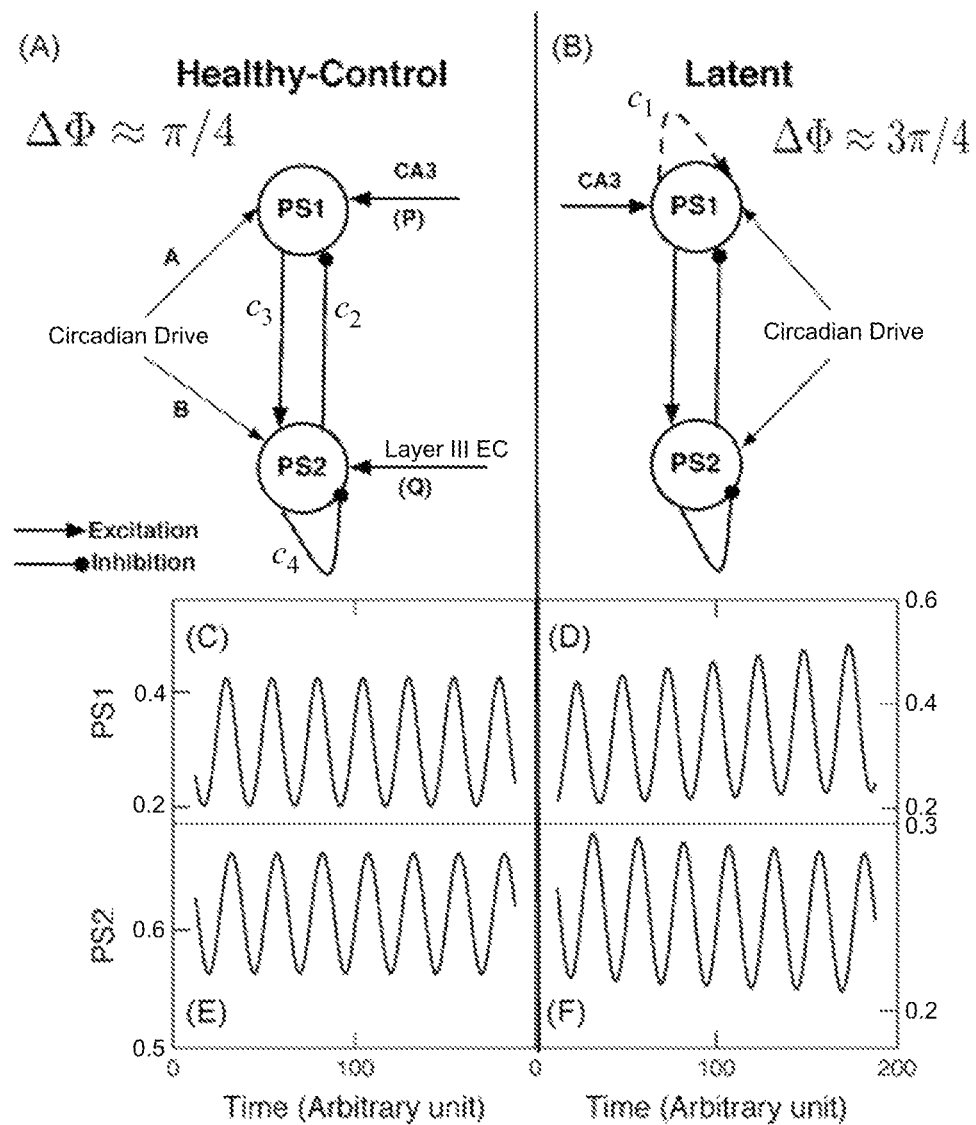
Fig. 12A-F

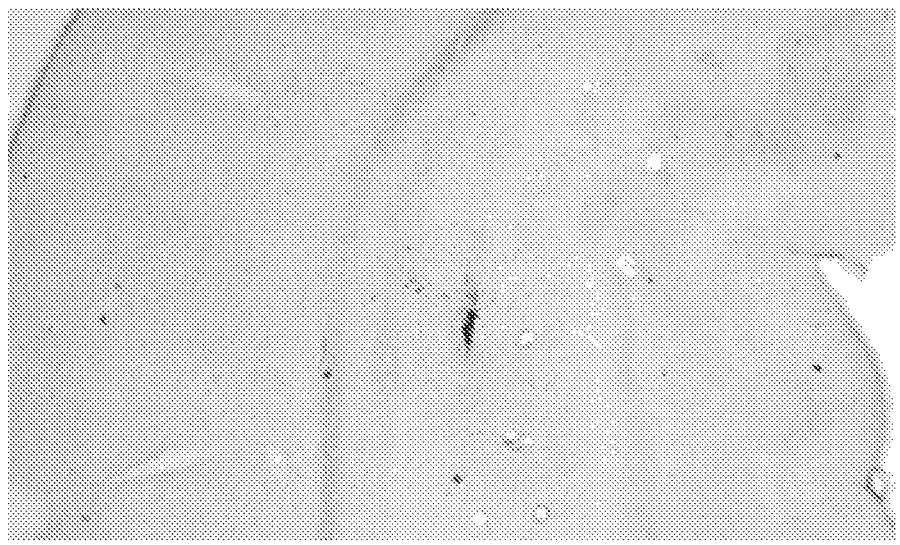
Fig. 13
Fig. 14
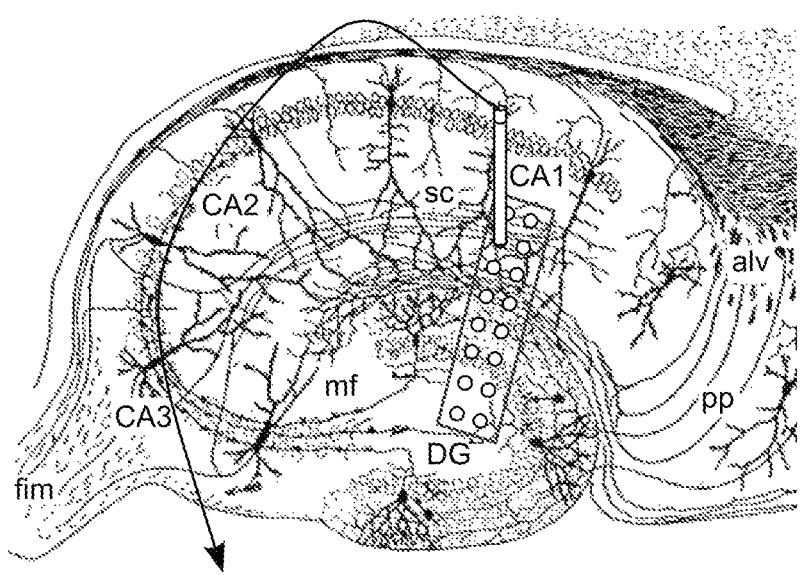

METHOD AND SYSTEM FOR DETECTING EPILEPTOGENESIS

CROSS REFERENCE TO RELATED APPLICATIONS

This application is a continuation-in-part of, and claims the benefit of, PCT Application PCT/US09/42452, filed Apr. 30, 2009, which in turn claims the benefit of U.S. Provisional Application Ser. No. 61/049,046, filed Apr. 30, 2008. The contents of each of the foregoing applications are hereby incorporated by reference in their entirety.

STATEMENT REGARDING FEDERALLY SPONSORED RESEARCH, AND JOINT RESEARCH AGREEMENTS

This research was supported by the National Institutes of Biomedical Imaging and Bioengineering (NIBIB) through Collaborative Research in Computational Neuroscience (CRCNS) Grant Numbers R01 EB004752 and EB007082, the Wilder Center of Excellence for Epilepsy Research, and the Children's Miracle Network. SST was partially funded by a Fellowship Grant from the Epilepsy Foundation of America. WLD was partially supported through the J. Crayton Pruitt Family Endowment funds. PRC was partially supported through the Wilder Center of Excellence for Epilepsy Research Endowment funds. The analysis work in this project was sponsored through a grant from the office of Naval research (Grant Number N00014-02-1-1019).

The U.S. Government has a paid-up license in this invention and the right in limited circumstances to require the patent owner to license others on reasonable terms as provided for by the terms of Grant Number N00014-02-1-1019 awarded by the Office of Naval Research, and Grant Numbers R01 EB004752 and EB007082, awarded by the National Institutes of Biomedical Imaging and Bioengineering (NIBIB) through Collaborative Research in Computational Neuroscience (CRCNS).

FIELD OF THE INVENTION

The invention relates to detecting the onset of an epileptic seizure sufficiently early to potentially eliminate or reduce the severity of the seizure.

BACKGROUND OF THE INVENTION

A fine balance between neuronal excitation and inhibition governs the physiological state of the brain. It has been hypothesized that when this balance is lost as a result of excessive excitation or reduced inhibition, pathological states such as epilepsy emerge. Decades of investigation have shown this to be true in vitro. However, in vivo evidence of an emerging imbalance during the "latent period" between the initiation of injury and the expression of the first spontaneous behavioral seizure has not been demonstrated.

"Balanced" networks in the brain have been proposed to account for a large variety of observations of cortical activity, including the representation of sensory information, decision making and sleep and motor control [7]. A loss of balance in the neuronal network activity has been associated with the emergence of a number of neurological diseases including Parkinson's [15], Autism [18], Schizophrenia [22], and Tourette's syndrome [20]. Epilepsy, a neurological disorder of the brain in which patients suffer from recurrent seizures, is associated with an imbalance in the activity of excitatory and inhibitory populations of neurons in the brain, in favor of the former, leading to an abnormal hyper-synchronous state of the brain [4]. A number of in vitro studies have demonstrated the mechanism of this hyper-excitability at the synaptic level [8,11]. However, the functional implication of these synaptic changes leading to the progression of the brain to an epileptic state following brain injury in an in vivo system is still unknown.

Epilepsy is the propensity to have seizures and is one of the most common serious neurological conditions, affecting 0.4% to 1.0% of the world population [24]. EEG recordings usually demonstrate interictal discharges (population spikes, sharp waves) over the hippocampal formation [25]. One of the major points of confusion in understanding the pathophysiology of epilepsy is the differentiation of a seizure from the interictal discharges. A seizure is a transient paroxysm of excessive discharges of neurons in the cerebral cortex causing a discernable change in behavior. Brief synchronous activity of a group of neurons leading to a population spike shares some mechanisms with seizure generation; spikes should, however, be recognized as a distinct phenomenon [26].

Spikes corresponding to both excitatory and inhibitory synaptic activities are significant features of network changes during epileptogenesis [27,28,29]. There remained, therefore, a need to further understand specific changes in excitatory and inhibitory synaptic balance and their relationship to epileptogenesis.

SUMMARY OF THE INVENTION

After the pioneering use of microelectrodes during the 1940's [30], several groups started to record local field potentials to understand the patterns of excitation and inhibition in the hippocampus. Local field potentials represent the coordinated synaptic activity in the population of the neurons. The recorded high amplitude field potentials also referred to as "population spikes" ("PS") reflect the synchronized synaptic activity of the population of neurons firing together in a local area surrounding the recording electrode. Two main factors govern the shape and sign of the population spikes from the hippocampus [31]. First, neurons in the hippocampus are organized in laminar fashion with parallel position of the apical dendrites. The cell bodies in the hippocampus are densely packed and can be easily synchronized. When these neurons receive excitatory input into their cell bodies, the result is for the current to flow into the cell bodies and produce an active current sink in the measured field potential in the extracellular space.

In accordance with the invention, this pattern of high amplitude population spikes corresponding to the summated population EPSP is termed the field excitatory postsynaptic potential (fEPSP, or PS1). Second, coherent extracellular current flow resulting from synchronous interneuronal firing will produce an active current source in the measure field potential in the extracellular space. Population IPSPs corresponds to the largest component of current flow through the hippocampal pyramidal cells [32]. This population spike corresponding to the summated population IPSP is referred to as field inhibitory postsynaptic potential (fIPSP, or PS2).

The invention demonstrates an emerging imbalance between excitation and inhibition in vivo by employing long term, high temporal resolution, and continuous local field recordings from microelectrode arrays implanted in an animal model of limbic epilepsy. The inhibitory and excitatory postsynaptic field activity were tracked during the entire latent period, from the time of injury to the occurrence of the first spontaneous epileptic seizure. During this latent period, a sustained increase in the firing rate of the excitatory postsynaptic field activity was observed, paired with a subsequent decrease in the firing rate of the inhibitory postsynaptic field activity within the CA1 region of the hippocampus. Firing rates of both excitatory and inhibitory CA1 field activities followed a circadian or circadian-like rhythm, which is locked near in-phase in controls and near anti-phase during the latent period. The invention identifies observed changes as biomarkers for the occurrence of spontaneous seizure onset following injury.

The invention examines excitatory and inhibitory synaptic activity as significant features of network change during epileptogenesis. In accordance with the invention, the evolution of extracellular field potentials corresponding to the excitatory and inhibitory synaptic activity over the entire period from the time of injury up to the onset of epileptic seizures are observed and characterized, in particular with respect to changes in excitatory and inhibitory synaptic balance, which changes are used as biomarkers for detecting epileptogenesis.

In one embodiment of the invention, long term, high temporal resolution, and continuous local field recordings are taken from implanted microelectrode arrays. Tracking is carried out for inhibitory and excitatory postsynaptic field activity during the entire latent period, from the time of injury to the occurrence of the first spontaneous epileptic seizure.

In accordance with the invention, at least six biomarkers indicating epileptogenesis are identified.

In accordance with a first biomarker, during the latent period, a sustained increase in the firing rate of the excitatory postsynaptic field activity is observed, paired with a subsequent decrease in the firing rate of the inhibitory postsynaptic field activity within the CA1 region of the hippocampus.

In accordance with second and third biomarkers, the mean amplitude profiles of both fEPSP and fIPSP field potential activity during the latent period have characteristic shapes, respectively.

In accordance with a fourth biomarker, both excitatory and inhibitory CA1 field activity firing rates are observed to follow a circadian rhythm that drifts during epileptogenesis.

In accordance with a fifth biomarker, the circadian rhythms described are in-phase in controls and anti-phase during epileptogenesis.

In accordance with a sixth biomarker, the fEPSP rate drifts from a circadian rhythm to a greater extent than the fIPSP rate.

Any or all biomarkers may be monitored in accordance with the invention to assist in the prediction of the occurrence of spontaneous seizure onset, for example following injury, or otherwise as a result of neurological predisposition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 5A-D illustrate a circadian modulation in the firing rates of the fEPSP and fIPSP field potentials, FIGS. 5A-B illustrating normalized firing rates, and FIGS. 5C-D the firing rates of a poststatus epilepticus study subject;

FIGS. 6A-B illustrate the phase relationship of the circadian modulation of the firing rates between the two field potentials during control and latent periods;

FIGS. 7A-B illustrate the average number of fEPSP and fIPSP events per hour for control and for poststatus epilepticus latent periods;

FIG. 8A illustrates the mean amplitude of the drift in firing rate for fEPSP and fIPSP activity from all study subjects during three time periods of prestatus epilepticus, and in control subjects;

FIG. 8B illustrates the phase of the circadian like oscillations of the fEPSPs and the fIPSPs represented by the time when the firing activity per day reaches its maximum;

FIGS. 9A-C illustrate a normalized cross-correlogram represnting the probability of observing a fIPSP event within an interval in minutes of a fEPSP event for the prestatus, latent and sham control periods;

FIG. 10A illustrates a representative example deomonstrating the procedure used to determine the drift D in the firing rate of fEPSP and fIPSP field activities;

FIG. 10B illustrates a representative example demonstrating the procedure used to determine the phase of oscillations in the firing rates of fEPSPs and fIPSPs;

FIG. 11 represent a flowchart for the extraction of the fEPSP and fIPSP field potentials, where FIG. 11A is a sample EEG trace;

FIG. 11B is a raster plot of the spike events pooled over a period of 24 hours of continuous EEG recordings;

FIG. 11C illustrates pooled spike events normalized in amplitude and peak-adjusted;

FIG. 11D illustrates the output of the clustering procedure resulting in three separate clusters;

FIG. 11E illustrates the two primary clusters representing the fEPSP and the fIPSP field potentials;

FIG. 11F shows the probability-density plots of the spike patterns of the clustering procedure of FIG. 11D;

FIG. 11G shows the corresponding spike patterns represented in the probability density plots of FIG. 11E;

FIGS. 12A-F are diagrams of the interactions between the PS in controls and in epileptogenic rats;

FIG. 13 illustrates a histological slice of a brain, showing the electrode placement, revealed staining for iron;

FIG. 14 illustrates a schematic diagram of the hippocampus and the location of the implanted electrode array;

DETAILED DESCRIPTION OF THE INVENTION

In the description which follows, the particular embodiments described herein are not to be considered as limiting of the present invention.

To look for an imbalance between inhibitory and excitatory spike wave discharges, the invention concentrates on the CA1 region during epileptogenesis since a number of in vitro studies have shown that there exist global changes toward more glutamatergic and less GABAergic activity in the CA1 region, resulting in the net increase in the excitability of the CA1 network during epileptogenesis [28,11,33].

Temporal dynamics of firing rate were observed, of a high amplitude short time duration (100-200 ms), hereinafter referred to as population spikes ("PS"). The PS are the macroscopic physiological features representing the integrated synaptic activity in the extracellular space generated by synchronous firing of populations of neurons in the brain [3] and [5]. Depending on the shape profile two distinct classes of PS were identified in neural recordings from the hippocampal CA1 area, labeled as type 1 PS (PS1, or fEPSP) with a large negative excursion in the measured electrical activity and type 2 PS (PS2, or fIPSP) with a large positive excursion in the measured electrical activity.

The firing rates of the two PS (defined as the number of spontaneous PS events observed per unit of time) exhibit circadian-like 24 hour periodicity and are locked in-phase in control rats. However, during the latent period, defined as the time period following brain injury until the time of generation of first spontaneous epileptic seizures, while the firing rates of these PS are circadian, they are now locked in anti-phase. This phase shift is abrupt, occurring within a few days post-brain injury, and may occur as early as within one day after epilepticus inducing event (e.g. an injury or stimulus), and persists throughout the latent period. During the latent period, an evolving imbalance in the firing rate of the two PS (quantified through an estimate of the drift in the baseline firing rate), such that there is a sustained increase in the firing rate of PS1 with a concurrent sustained decrease in the firing rate of PS2. In accordance with the invention, this evolving imbalance may be implicated in the generation of the first spontaneous epileptic seizure following electrically induced status epilepticus, and is used as a marker of a potential seizure.

Figure 1:
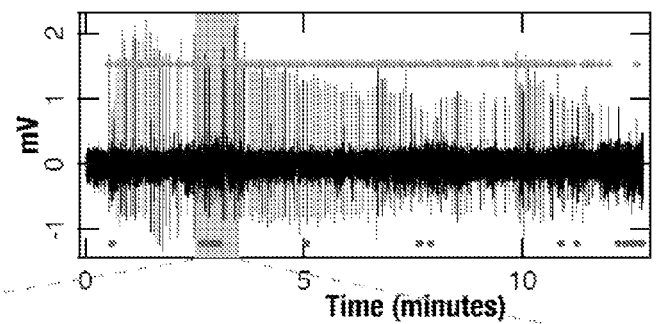
FIG. 1 illustrates a 12 minute segment of an EEG trace of a living brain, overlaid with fIPSP activity and fEPSP activity as upper and lower traces, respectively, detected through a clustering algorithm.
Figure 2:
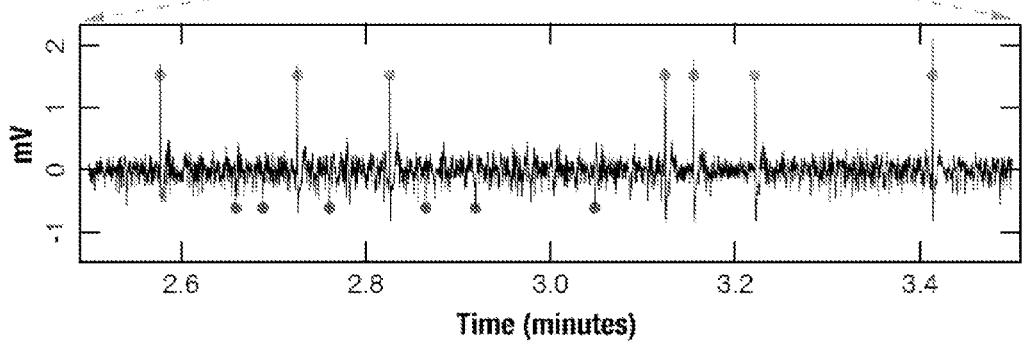
FIG. 2 illustrates an enlarged view of a one minute segment of the EEG trace of FIG. 1.
Figure 3:
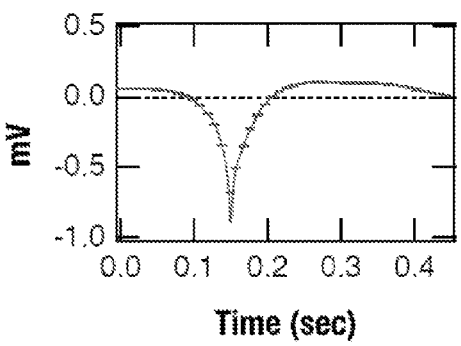
FIG. 3 illustrates a mean amplitude profile of fEPSP activity obtained from a sampling of fEPSP events during an observed latent period of a study subject.
Figure 4:
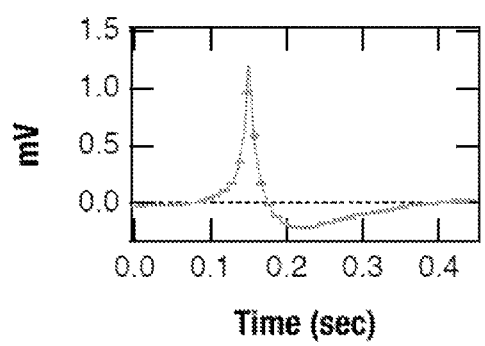
FIG. 4 illustrates a mean amplitude profile of fIPSP activity obtained from a sampling of fIPSP events during an observed latent period of the study subject of FIG. 3.
Figure 15:
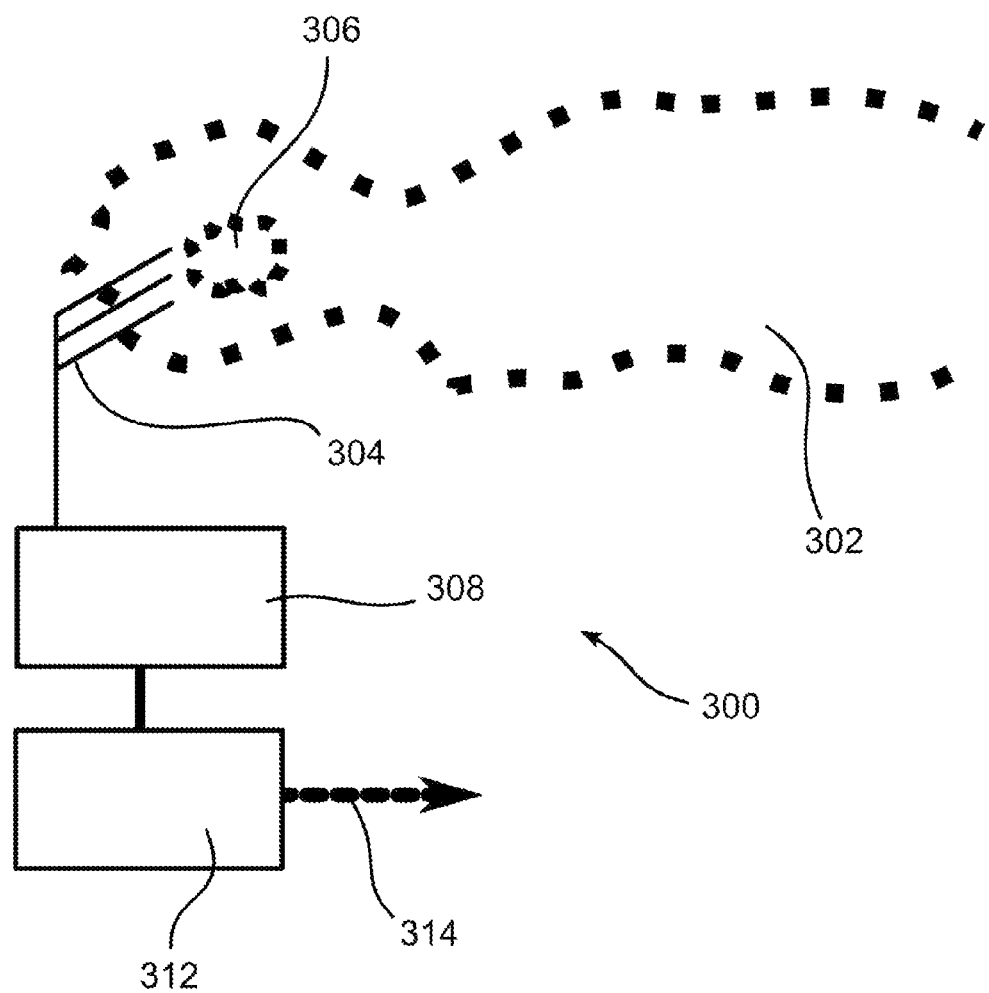
FIG. 15 illustrates a system in accordance with the invention for detecting and communicating epileptogenesis.
Figure 16:
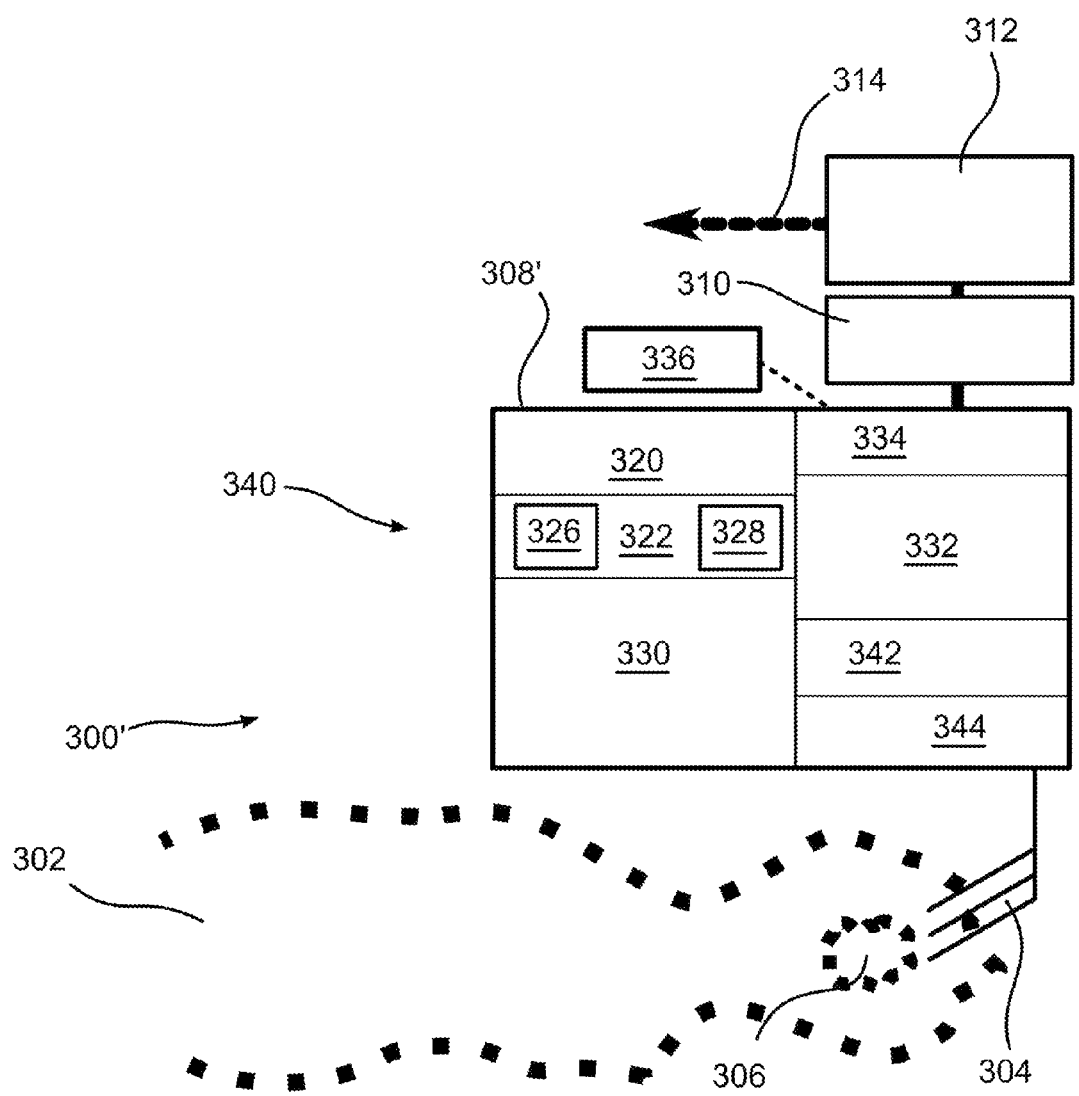
FIG. 16 illustrates an alternative system in accordance with the invention, for detecting and communicating epileptogenesis.

Local field potentials from CA1 were recorded and high amplitude field activity corresponding to inhibitory and excitatory postsynaptic potentials were extracted (See Methods and FIG. 11). A representative example of local field potential recorded with a microwire implanted in the CA1 is shown in FIGS. 1-2. FIG. 3 shows the mean shape of the fEPSP field potential activity (with standard error corresponding to 95% confidence interval) obtained from a total of about 40,000 fEPSP events detected over a period of 12 days of near continuous recordings during the latent period in a rat electrically stimulated into status epilepticus. FIG. 4 shows the mean shape of the fIPSP field potential activity (with standard error corresponding to 95% confidence interval) obtained from a total of about 24,500 fIPSP events detected over the same time interval in the same rat.

The time evolution of the normalized fEPSP and fIPSP firing rates from the age-matched sham controls and the epileptogenic latent period, are shown in FIGS. 5A-D. Key points observable in FIGS. 5-7 include: (1) the existence of a circadian-like (with period near 24 hour) modulation in the firing rate of the fEPSP and fIPSP field activity; (2) there is no observed drift in the firing rate of the fEPSP and fIPSP field activity in data obtained from sham control rats (FIGS. 5A and 5C); (3) during the latent period, there is a marked upward drift in the firing rate of fEPSP field activity and a corresponding marked downward drift in the firing rate of the fIPSP field activity (FIGS. 5B and 5D) (Biomarker 4); (4) the circadian-like modulation of firing rates of the fEPSP and fIPSP are locked near in-phase in sham control period (FIG. 6A) while during the latent period following status epilepticus the two field potentials oscillate near out-of-phase with respect to each other (FIG. 6B) (Biomarker 5); (5) Finally, the average number of fEPSP events per hour recorded during the latent period of epileptogenesis are significantly greater than that recorded during the sham control-period, while the average number of fTPSP events per hour are significantly less during the latent period as compared to the sham controls (FIGS. 7A-B) (Biomarker 1).

FIGS. 8-9 summarize the results on the imbalance in the firing rates and the phase reversal of the circadian-like oscillations of the fEPSP and fIPSP field potentials pooled across data collected from all rats. The imbalance in the firing rates is quantified by estimating the drift in accordance with the formula:

$$D = \left\langle \frac{\Delta f}{\Delta t} \right\rangle$$

where (f: firing rate) is the firing activity of both fEPSPs and fIPSPs through a least-squares fit of the firing rate data to a straight line, according to the formula:

$$\Delta f = D\Delta t + c$$

(See FIG. 10A). From FIG. 8A, it can be seen that, while the firing rates are in balance during the sham and prestatus control periods, the imbalance (as quantified by the difference in the drift rates of fEPSPs and fIPSPs) is significantly higher during the poststatus latent period ($p \approx 0.0044$, two sample t-test). The phase relationship between the circadian like firing activity of the fEPSPs and fIPSPs is quantified through a least sqaures-fit of the detrended-modulo 24 firing rate data with a sinosidual function $$f(t) = a \sin(\omega t + b),$$

with $$\omega = 7.2722 * 10^{-5} \text{ Hz}$$

(See FIG. 10B). The phase is associated with the time $$T_X^M$$

(X=fEPSP,fIPSP) of maximum value obtained by $f(t)$. The phase of fEPSP and fIPSP oscillations are shown in FIG. 8B. The relative phase difference is quantified as $$\Delta T = |T_{fEPSP}^M - T_{fIPSP}^M|$$

It can be seen that during the control period, the two field potentials are phase-locked with a lag of around 3 hours, however during the latent period the phase lag increases to approximately 9 hours (Biomarker 6). It is observed, in accordance with the invention, that due to the large relative phase shift in the oscillations of the fEPSPs and fIPSPs during the latent period the increase in firing rate of fEPSPs is not compensated by subsequent increase in the fIPSP firing activity and as a result, an emerging state of imbalance in the firing rates occurs during the latent period, making the network within the CA1 increasingly excitable and eventually triggering the first spontaneous epileptic seizure.

Finally, FIGS. 9A-C shows the normalized cross-correlogram (NCC) of the fIPSPs with respect to fEPSPs for the sham control, prestatus epilepticus control and the poststatus epilepticus latent periods. The NCC represents the probability of observing a fIPSP event over time interval [−T,T] around an fEPSP event. During the control periods (FIGS. 9A-B), the timing of occurrence of the two field potentials are highly correlated with fIPSP activity leading fEPSP activity on average. However during the poststatus epilepticus latent period (FIG. 9C), we see a consistent dip in the NCC, with the minimum of NCC occurring at positive time values, suggesting the probability of firing of fEPSP event following an fEPSP event is decreased. These results suggest that the recurrent inhibition of pyramidal cells in the CA1 decreases resulting in a net increase in the excitatory field activity during the latent period.

Further in accordance with the invention, a circadian control is used as a biomarker, wherein the fine balance of synaptic activity of the fEPSPs and fIPSPs in healthy controls is under circadian influence, and are phase locked with respect to each other and injury such as electrical stimulation inducing status epilepticus, perturbs the phase relationship relative to the circadian rhythm, resulting in an imbalance in the firing rates of the fEPSPs and fIPSPs. The imbalance in turn produces an increasingly excitable CA1 network during the latent period of epileptogenesis.

The invention provides an additional biomarker through quantification of the evolving imbalance between the fEPSPs and fIPSPs following status epilepticus.

Example

Local field potentials were recorded using a chronically implanted microwires (50 μm polyimide insulated tungsten) in the hippocampal CA1, CA2 and the dentate gyms. Out of a total of five rats, three rats were electrically stimulated into status epilepticus by injecting a bi-phasic current pulse through a bipolar twist stainless-steel electrode implanted in the ventral hippoampus. Continuous EEG/video data were collected at a high sampling rate of 12 KHz. In house software was used to save the recorded data in a 16-bit binary format for later processing. The schematic flow chart of the data analyzed to extract the excitatory and inhibitory field potentials is given in FIGS. 11A-G. All the figures were generated using custom programs within IGOR Pro (WaveMetrics, Inc).

Method Detail

The following method may be used for demonstrating biomarkers in accordance with the invention:

Animal Surgery and Electrode Implantation.

Experiments were performed on 2-months old male Sprague Dawley rats (n=9) weighing 200-265 g. The Institutional Animal Care and Use Committee of the University of Florida approved all protocols and procedures (IACUC protocol D710). The rats were induced into the state of complete anesthesia by subcutaneous injection of 0.1 mm/L of xylazine and maintained in the anesthetized state using isoflurane administered through inhalation by a precision vaporizer. In three of the five rats, a bipolar, twisted, Teflon-coated, stainless steel electrode (330 um) was implanted in the right posterior ventral hippocampus (5.3 mm caudal to bregma, 4.9 mm right of midline suture and at a depth of 5 mm from the dura) for stimulating the rat into status epilepticus. In all the five rats a sixteen microwire (50 um) electrode array was implanted to the left of midline suture in horizontal fashion in the CA1-CA2 and the dentate gyms of the hippocampus. The furthest left microwire was 4.4 mm caudal to bregma, 4.6 mm left of midline suture and at a depth of 3.1 mm from the dura. A second microwire array of 16 electrodes was implanted to the right of midline suture in a diagonal fashion. The furthest right microwire was 3.2 mm caudal to bregma, 2.2 mm to the right of midline suture. The closet right microwire was 5.2 mm caudal to bregma, 1.7 mm to the right of midline suture and at a depth of 3.1 mm from the dura.

Induction of Status Epilepticus

Three of the 5 rats were electrically stimulated into status epilepticus by delivering a biphasic square wave stimulus trains at a frequency of 50 Hz and with a pulse duration of 1 ms and intensities of 300-400 uA continuously for 50-70 min with a duty cycle of 10 s on/2 s off. During the stimulus the usual behavioral response of the animal was the display of "wet dog shakes" and increased exploratory activity. After approximately 20-30 min of stimulation, convulsive seizures in the form of "wet dog shakes" (up to 1 min in duration) were usually observed about every 10 min. At the end of the stimulus period, continuous EEG recordings were observed for evidence of slow waves in all recorded channels. Upon termination of continuous hippocampal stimulation, the EEG continued to demonstrate activity below 5 Hz for 12-24 hr and intermittent spontaneous 30-60 s electrographic seizures for 2-4 hr. Animals were observed for seizure activity and adequate food and water intake for 12-24 hr after stimulation. Following behavioral stabilization, animals were returned to the vivarium for 4 to 6 weeks, during which time spontaneous seizures developed.

Data Acquisition.

The electrophysiological recordings were conducted by hooking each rat onto a 32-channel commutator, the output of which was fed into the recording system comprised of two 16-channel pre-amps, which digitizes the incoming signal with a 16 bit A/D converter at a sampling rate of 12 KHz. The digitized signal was then sent over a fiber optic cable to a Pentusa RX-5 data acquisition board (Tucker Davis Technologies), where the signals were bandpass filtered between 1.5 Hz and 7.5 kHz. The bandpassed digital stream of data was then stored in binary format for later processing.

Data Analyses for Spike Extraction.

We analyzed single channel data from microwire electrode implanted in the hippocampal CA1 ipsilateral to the stimulation electrode. High amplitude local field activity corresponding to inhibitory and excitatory postsynaptic potentials were extracted using the following methodology: Complete data sets from each rat were divided into non-overlapping 1 hr time windows to ensure a lack of drift in the amplitude of the EEG signal. Candidate events, representing those events from the recorded data whose amplitude exceeds a threshold of five standard deviations ($5\sigma$) from the median of the absolute value of the EEG signal in the 1 hr window were extracted. This multiple of the standard deviation used to establish the threshold for extracting candidate events was determined by measuring the multiple of the standard deviation where the numbers of events first plateau before decreasing again to zero from a random sampling of 1 hr windows over the entire experiment. The peak of each event was determined from a polynomial fit of a region around the maximum amplitude of the data in a window of 1.5 s duration centered on the threshold crossing. Data from the temporal window that best captured the entire profile of the candidate event was extracted. This consisted of a time window of 0.45 s centered on the event including 0.15 s before the fitted peak to 0.3 s after the fitted peak. Then these peak-aligned candidate events were sorted using a modification of a well-established clustering algorithm 16 to generate two primary clusters representing the excitatory and inhibitory field potential activities.

To confirm electrode placement, a 3-dimensional, gradient echo MR image was acquired at 17.6 T (750 MHz) with a Bruker Avance system (Bruker NMR Instruments, Billerica, Mass.). The fixed brain was excised intact, washed overnight in saline, and then imaged in fluorinated oil. The image was acquired with a recovery time of 150 ms, an echo time of 15 ms, using 2 averages and a resolution of 75 microns in each direction. Orthogonal slices were taken, with the tip location terminating in CA1. The complete three-dimensional image volume illustrated an electrode tract within the brain. The electrode tract was visible in the MR image because iron, accumulated around the site of electrode insertion, shortens the MR transverse relaxation time.

Using another rat brain treated in the same way, the presence of iron is confirmed in the histological slice in FIG. 13, which was prepared using Perl strain with diamine-benzidine-tetrahydrocloride. In this slice, the iron surrounding a tract is visible as the black region in the middle of the slice. FIG. 14 shows a schematic diagram of the hippocampus and the location of the implanted electrode array (blue box and circles in the box).

FIG. 2 shows a sample EEG trace of 3 minutes duration from recordings obtained during the latent period in one of the electrically stimulated rats. Overlaid over the raw EEG trace in green represents the time of fIPSP field potential activity and in red represents the time of fEPSP field potential activity, detected through the clustering algorithm.

FIG. 3 shows the mean amplitude profile of the fEPSP field potential activity (with standard error representing 95% confidence level) obtained from a total of 40000 fEPSP events over the entire latent period of recordings from the same rat electrically stimulated in status-epilepticus (Biomarker 2).

FIG. 4 shows the mean amplitude profile of the fIPSP field potential activity (with standard error representing 95% confidence level) obtained from a total of 24,500 fIPSP events over the same period (Biomarker 3).

With reference to FIGS. 5-7, A representative example demonstrating circadian modulation in the firing rates of the fEPSP and fIPSP field potentials is illustrated. FIGS. 5A-B show the time evolution of the normalized firing rates of the fEPSP field potentials from EEG data obtained from sham-control rat C1 and during the poststatus epilepticus latent period in rat E2.

FIGS. 5C-D show the time evolution of the normalized firing rates of the fIPSP field potentials from EEG data obtained from the same two rats. The time of the first spontaneous seizure following the latent period is marked in dotted blue line. Solid red line (fEPSP) and solid green line (fIPSP) represent a least-squares fit of the firing rate data to a function of the form, $f(t)=at+b\sin(ct+d)+e$. The diurnal cycle is shown in the background with gray shaded region representing the controlled dark cycle and the white region representing the controlled day cycle.

The phase relationship of the circadian modulation of the firing rates between the two field potential activities during the sham-control and the latent periods are shown in FIGS. 6A and 6B, respectively. The diurnal cycle is again represented in the background. The average number of fEPSP and fIPSP events per hour over the entire duration of the sham-control period in rat C1 and the poststatus epilepticus latent period, in rat E2 are shown in FIGS. 7A and 7B.

With reference to FIG. 8A, the mean amplitude of the drift in the firing rate, D, of the fEPSP field potential activity and the drift in the fIPSP field potential activity in data from all the recorded rats during the three time periods of prestatus epilepticus (Prestatus), post status epilepticus latent period (Latent) and the sham-control (Sham) are shown with the standard error representing 95% confidence level. The rightmost figure shows the rate of divergence or the imbalance in the two field potential activities, as represented by the difference in the mean amplitude of the drift in the firing rates is shown. The standard error in this case represents the maximum and the minimum difference between the two field potential activities.

In FIG. 8B, the phase of the circadian like oscillations of the fEPSPs and the fIPSPs represented by the time in hours $T^M_X$ (X=fEPSP, fIPSP) when the firing activity per day reaches its maximum is shown. The standard error corresponds to the 95% confidence interval. The relative phase shift as quantified by the difference $\Delta T=|T^M_{fEPSP}-T^M_{fIPSP}|$, is shown in the rightmost figure.

Normalized cross-correlogram representing the probability of observing a fIPSP event in time interval of [−60:60] minutes of a fEPSP event for the prestatus, latent and the sham control periods are shown in FIGS. 9A, 9B and 9C, respectively.

FIGS. 11A-G illustrate a flowchart for the extraction of the fEPSP and fIPSP field potentials. FIG. 11A shows a sample EEG trace of one hour in duration from a single microwire electrode implanted in the CA1, obtained during the latent period of recordings from one of the rats induced into status epilepticus.

FIG. 11B shows a raster plot of the spike events pooled over a period of 24 hours of the continuous EEG recordings. The pooled spike events represent the set of spike events selected from a non-overlapping time window of one hour of the EEG data, whose amplitude exceeds a threshold of 5σ, where σ is the standard deviation computed for each one hour of recordings of the EEG data.

In FIG. 11C, pooled spike events are then normalized in amplitude, and peak-adjusted to discount for any large amplitude fluctuations and jitter in timing of the rastered spike events before feeding them into the automated clustering algorithm [12].

FIG. 11D shows the output of the clustering procedure resulting in three separate clusters (show in black, blue and red) with the corresponding probability-density plots of the spike patterns are shown.

FIG. 11E shows the two primary clusters representing the fEPSP (red) and the fIPSP (blue) field potentials and the corresponding spike patterns represented in the probability density plots. The final two spike patterns are selected by determining the cross-correlation of the events in the third cluster (black) with the mean shape-profiles of the events in the two primary clusters. Only those events in the cluster (shown in black) whose cross-correlations is >75% are included in one of the two final primary spike clusters representing the fEPSPs and the fIPSPs.

FIGS. 10A-B illustrate a procedure to determine the drift in the firing rate and the phase of circadian-like oscillations of the firing rates of the fEPSP and fTPSP field potentials. FIG. 10A shows a representative example demonstrating the procedure used to determine the drift D in the firing rate of fEPSP and fIPSP field activities. Shown in black dotted points, are the firing rates of the fEPSP field potential events, extracted from continuous EEG recordings during the sham-control period, determined from a moving time window of one hour with an overlap of 10 minutes. The total time duration and the firing rate magnitude are normalized to scale between [0, 1]. Solid red line represents the least-squares fit to the magnitude-time normalized firing rate data with the function of the form $f(t)=Dt+b$, where D represents the drift in the firing rate data. The dotted blue lines represent the 95% confidence-bound for the fitted data.

FIG. 10B shows a representative example demonstrating the procedure used to determine the phase of oscillations in the firing rates of fEPSPs and fIPSPs. Shown in black dotted points are the modulo 24, detrended and normalized firing rate data obtained from the fEPSP events selected over the sham-control period of continuous EEG recordings. The firing rates are determined over a moving time window of 6 hours with an overlap of 5 hours. The drift in the firing rate data is removed following the procedure described for FIG. 10A. The detrended (after removing the drift) firing rate data is then normalized to scale between [0, 1] and rastered over a time window of 24 hour (modulo 24). Least squares fit of the modulo-24, detrended and normalized firing rate data with a function of the form $f(t)=a \sin(\omega t+b)$, with $\omega=7.2722*10^{-5}$ Hz is shown in red. The dotted blue lines represent the 95% confidence bounds on the fitted data. The phase of oscillation is then associated with the time of the maximum reached by the function $f(t)$ over a time period of 24 hours.

Analysis

The experiment used adult male Sprague Dawley rats (n=9) of age 63 days and weighing between 200 and 265 g, implanted with 16 microwire recording electrodes (microelectrodes) bilaterally into the CA1 and the dentate gyms regions of the hippocampus. In addition, a bipolar, twisted Teflon-coated stainless steel electrode was implanted into the right ventral hippocampus for the induction of brain injury [16]. After 1 week of baseline recordings at a sampling rate of 12 kHz, rats (n=7) were electrically stimulated for 30 min until sustained behavioral and electrographic seizures were observed. After the rats stopped seizing they entered a seizure-free latent period. Subsequently, rats were housed in a controlled environment with 24 h symmetric day-night cycle and monitored with continuous video and extracellular brain electrical activity recordings. Videos were screened daily for spontaneous seizures. At the end of the recording session, the rats were sacrificed and the intact brains were excised. The isolated intact brains were imaged with high-field magnetic resonance microscopy to confirm the location of the electrode placement within the CA1 region of the hippocampus [19] and [21]. In total 7 (E1-E7) rats were electrically stimulated into status epilepticus. A total of 3 rats (E1-E3) entered the chronic phase of epileptic seizures, following an epileptogenic phase with a minimum of a Racine grade 3 first spontaneous seizure. Data presented in this work is primarily derived from these 3 epileptogenic rats. The rats (E4-E7) provided us with additional data-points to validate epileptogenic circadian modulation in firing activity of PS events following status epilepticus.

FIG. 4 illustrates a representative example of the extracellular activity recorded from the hippocampal CA1 area of an epileptogenic rat during the latent period. Overlaid on the trace, in squares and circles, is shown the PS1 and PS2 events, respectively. In FIGS. 3 and 4, the mean shape profile of the PS1 activity and the mean shape profile of the PS2 activity are illustrated, detected from the same rat over a latent time period of 12 days of recordings using a modification of a well-known spike clustering algorithm [12].

The time evolution of the normalized firing rates of PS1 and PS2 from an age-matched control rat (C1) and during the latent period in an epileptogenic rat (E2) is shown in FIGS. 6A-D. FIGS. 5-7 illustrate: (1) there exists a circadian-like modulation in the firing rate of the PS1 and PS2 activity both during the control and the latent time periods; (2) there is no observed drift in the firing rate of the PS1 and PS2 activity in the data obtained from control rats (FIGS. 5A and C); (3) during the latent period there is a marked upward drift in the firing rate of PS1 and a corresponding marked downward drift in the firing rate of the PS2 (FIGS. 5B and D); (4) the circadian-like modulation of firing rates of PS1 and PS2 are locked in-phase during the control period (FIG. 6A), while during the latent period the two PS oscillate anti-phase with respect to each other (FIG. 6B), with a marked shift in the rhythmic activity of PS1; (5) the average number of PS1 events per hour recorded during the latent period in the three epileptogenic rats are significantly greater ($p\approx0.0026$; two-sample t-test) than that recorded during the control period, while the average number of PS2 events per hour are less ($p\approx0.058$; two-sample t-test) during the latent period as compared to the pre-status epilepticus control period in these rat (FIGS. 7A and B).

FIGS. 5A-D illustrate the firing rates of type 1 (PS1) and type 2 (PS2) population spikes recorded from a control rat (C1) and an epileptogenic rat (E2) during the latent period. Red dotted lines represent the least-squares fit of the firing rate data to a function $f(t)=at+b \sin((t+c)$ where $\omega=7.2722\times 10^{-5}$ Hz. The fitted line is shown as a guide for the eye to follow the circadian pattern in the firing activity of PS. The gaps in the firing rate data (around day 5 in both control and latent period) reflect the absence of recordings on those days due to technical problems. The phase of circadian oscillations of PS1 and PS2 from the control rat and the epileptogenic rat are shown in FIGS. 6A and 6B, respectively. The red line is a least squares fit to the phase data with a function $f(t)=\alpha \sin(\omega t+\beta)$, where $\omega=2\pi$. The diurnal day-night cycle is shown in the background. The dotted line in (B) and (D) shows the time of occurrence of the first spontaneous epileptic seizure. The average number of PS1 and PS2 events observed per hour during the pre-status epilepticus control time period and the epileptogenic latent period in rat E2 are shown in FIGS. 7A and 7B.

FIG. 8 summarizes the results on the phase shift in the circadian-like firing activity of the two PS and the imbalance in their firing rates during the latent period from the PS data obtained from 3 epileptogenic (E1, E2, E3) and 2 controls (C1, C2). The mean amplitude of the drift in the firing rate, D and the circadian phase shift in the relative firing activity of the type 1 (PS1) and type 2 (PS2) population spikes during the control and the latent periods are shown in (A) and (B), respectively. The imbalance in the firing rates is quantified by estimating the drift D=(df/dt) (f: firing rate) in the firing activity of both PS1 and PS2 through a least squares fit of the drift in the baseline-firing rate to a straight line, $\Delta f=D \Delta t+c$. FIG. 8A plots the mean value of D (with error bars representing the standard error corresponding to 95% confidence interval). FIG. 8A illustrates that, while the firing rates are in balance (D≈0) in controls, D>0 during the latent period in epileptogenic rats ($p\approx0.0044$, two-sample t-test). This implies an evolving imbalance in the firing activity of the two PS. The phase relationship between the circadian like firing activity of the PS1 and PS2 is quantified through a least squares-fit of the detrended-modulo 24 firing rate data (detrending implies the removal of the drift in the baseline of the circadian-like rhythm of firing rate) with a sinusoidal function $f(t)=\alpha \sin(\omega t+b)$, with $\omega=7.2722\times10^{-5}$ Hz. The phase is associated with the time $T_X$ (X=PS1, PS2) of maximum value obtained by $f(t)$ and is given as: $\Phi_X=2\pi T_X/24$. The mean value of phase for the two PS (with standard error corresponding to 95% confidence interval) is shown in FIG. 8B. The relative phase difference is quantified as $\Delta\Phi=|\Phi_{PS1}-\Phi_{PS2}|$. In-phase firing activity of the two PS is considered to occur when $\Delta\Phi\leq\pi/2$. As can be seen during the control period, the two PS events are phase-locked with a lag of around $3\pi/4$ radians, however during the latent period, the phase lag increases to approximately $3\pi/4$ radians. The phase shift $\Delta\Phi$ in the relative phase for the epileptogenic rat is significantly greater than that for the control rat ($p\approx7.3775\times10^{-5}$, two-sample t-test).

Based on these experimental findings, it may be hypothesized that the strength of the interactions between the populations of neurons in the hippocampus is dependent on their phase relative to the daily circadian cycle. Brain injury abruptly disturbs the circadian phase, which in turn triggers homeostatic mechanisms [9] producing changes in the interaction strength between the populations of hippocampal neurons which in turn modulates their firing activity. In accordance with the invention, this is referred to as the "circadian-control" (CC) hypothesis. Although the correctness of the hypothesis is not critical to carrying out the invention, it is presented here as an aid to the reader in understanding the invention. Accordingly, it is suggested that this may underlie the cause for the emerging imbalance in the firing activity of the PS in the hippocampal CA1 area.

A simple two-dimensional Wilson-Cowan model may be considered for the interaction between the PS1 and PS2 activity. The Wilson-Cowan model describes the dynamics of interaction firing activities of populations of excitatory and inhibitory neurons [23]. Reference may be had to FIGS. 12A and B, illustrating a schematic diagram of the interactions between the PS in controls and the epileptogenic rats, under the assumption that PS1 and PS2 represent the synchronous firing of populations of excitatory and inhibitory neurons, respectively.

More particularly, FIGS. 12A and 12B present the schematic diagram of the interaction between the type 1 (PS1) and the type 2 (PS2) population spikes in control and the latent period. The PS1 and PS2 firing activity generated by the model (Eq. (1)) for the control and the latent period are shown in FIGS. 12C and 12D. The model parameters are, A=0.5, B=0.25, $\omega=2\pi/25$, $T_x=T_y=1$, $T_L=200$, and p=0.025 for both the control and the latent time periods. Q=1.9 for control period and Q=0 for the latent time period.

Two specific assumptions are made in the development of our modified version of the Wilson-Cowan model for PS1 and PS2 interactions. (1) PS1 represents the synchronous firing of populations of excitatory neurons. This assumption is based on the observation that the firing rate of PS1 during the latent period of epileptogenesis increases as one gets nearer in time to the first spontaneous seizure. (2) PS2 events represent the synchronous firing of population of inhibitory neurons. This assumption is based on the observation that the firing rate of PS2 decreases during the latent period of epileptogenesis. These assumptions allow the incorporation of anatomical connectivity patterns, within the CA1 region [10], [13] and [14], into the model to test our hypothesis that the relative shift in the circadian phase results in a sustained increase in the firing rate of PS1, and a concurrent decrease in the firing rate of PS2. However, it is noted that the experimental approach of continuous long-term in vivo recording using a chronically implanted microwire electrode array precludes conclusively demonstrating the synaptic origin of the population spikes reported here. In summary, epileptic seizures are known to be associated with increased excitability within the CA1 pyramidal cells. Thus, the association of PS1 patterns with excitation and the PS2 pattern with inhibition conforms to the notion of increased excitation within the hippocampus resulting in the development of spontaneous epileptic seizures. If, then, within the framework of this modified Wilson-Cowan model, a coupled pair is taken, of ordinary differential equations (ODEs) governing the evolution of X(t) and Y(t) representing the firing rates of PS1 and PS2, respectively, we have:

$$t_x \frac{dX}{dt} = -X + S(A\sin(\omega t + \Delta\Phi) + c_1 X - c_2 Y +$$
$$t_y \frac{dY}{dt} = -Y + S(B\sin(\omega t) + c_3 X - c_4 Y + Q)$$
Equation 1 where $T_x \ll \omega^{-1}$ and $T_x \ll \omega^{-1}$. $S(x)=[1+\exp(-\alpha x)]^{-1}$ is the response function [23]. $c_j$ (j=1 ... 4) represents the strength of local interactions between the population of excitatory and inhibitory neurons in the CA1 area. The necessary condition for the coupled pair of ODEs in Eq. (1), to exhibit intrinsic stable limit cycle in absence of external sinusoidal driving (A=B=0) is, $c_1 \neq 0$ [17]. However, based on assumptions herein (See FIGS. 12A and 12B), $c_1$ represents the recurrent interaction between populations of excitatory neurons in the CA1 area that give rise to the PS1 activity. Moreover, it is known from the anatomy of network connectivity within the CA1 network, there are sparse recurrent connections between the CA1 excitatory neurons [13]. Additionally, the synaptic time scale of interaction between the populations of neurons in the CA1 is much faster than the circadian-like activity of PS (FIGS. 5-7). Therefore, in modeling of the firing activity of the two PS through Eq. (1) above, it is assumed that the origin of circadian-like oscillations in the hippocampal CA1 is from an external source. Although there might not be any direct anatomical pathway into the CA1 through which the circadian drive can influence the CA1 activity, there is evidence for the influence of a circadian cycle or drive on synaptic activity within the CA1 [2] and [6].

The invention models the circadian influence in Eq. (1) through an external sinusoidal input to X and Y. A and B represent the strength of external circadian drive onto both PS1 and PS2 activity, respectively, and $\Delta\Phi$ represents the phase difference in the time of circadian drive to the two classes of population spikes that are modulated following brain injury. P represents the excitatory input from the hippocampal CA3 Shaffer collateral-commissural projections onto the CA1 excitatory neurons [1]. Q represents the excitatory input onto the CA1 interneurons via the temporoammonic pathway from the layer III of the entorhinal cortex [14].

Finally, according to the CC hypothesis, the asymptotic strength of interaction between the PS1 and PS2 activity, $c_j^\infty$ is considered to be dependent on the phase-lag $\Delta\Phi$ of the circadian input that drives the PS1 and PS2 firing activity. The asymptotic strength of the interaction terms is modeled through a linear dependence on $\Delta\Phi$, $c_j^\infty = \alpha_j + \beta_j \Delta\phi$ and the differential equation governing the evolution of $c_j$ is given by $dc_j/dt = (c_j^\infty - c_j)/T_L$, where $T_L \ll \omega^{-1}$. The parameters used in our simulation example are ($\alpha 1, \alpha 2, \alpha 3, \alpha 4$)=(0.65, −0.015, 0, 0.32) and ($\oplus 1, \beta 2, \beta 3, \beta 4$)=(0, 0.05, 0.1, 0.5). FIGS. 12C-F illustrate the output from the model, simulating the conditions from the experimental findings (FIGS. 5-8). For $\Delta\Phi=3\pi/4$, representing the condition observed in controls (FIGS. 5A and 5C), it can be seen from FIGS. 12C and 12E that the firing rates of both PS1 and PS2 exhibit circadian rhythmicity with the maintenance of balance in the relative firing rate of two patterns. During the latency period, there is a sudden shift in the phase of circadian drive onto two populations of interacting neurons resulting in $\Delta\Phi=3\pi/4$. This, in turn, results in modulation in the interaction terms $c_j$ through the homeostatic learning rule. Additionally, due to the selective loss of neurons in layer III of the entorhinal cortex in the animal model of limbic epilepsy [10], parameter Q=0. As a result, there is a sudden decrease in the firing rate of PS2 activity. The non-linear interaction between the firing rates of PS through Eq. (1), then results in further decrease in firing activity of PS2 and a corresponding increase in the firing rate of PS1 activity (FIGS. 12D and 12F). Thus, using the constraints imposed through the CC hypothesis and the anatomy of network connectivity within the CA1, this simple model (Eq. (1)) is able to replicate our experimental finding of evolving imbalance in firing activity of the two PS following brain injury.

All the simulation results presented above were performed using a 4th order Runge-Kutta method for differential equations.

Experimental evidence is presented herein for an evolving imbalance in brain excitability following injury, as characterized by the firing activity of the two distinct classes of PS. The invention demonstrates that the imbalance in the PS firing rates is accompanied with a phase shift in the circadian rhythm of their relative firing activity. Based on this experimental observation a circadian control mechanism is proposed for the phase-induced imbalance in the observed firing activity of the two PS. The implications of the circadian control of PS activity is herein tested, using a modified two-dimensional Wilson-Cowan model. Although not critical to carrying out the invention, it is assumed that the recorded PS events in the hippocampal CA1 area represent interaction between excitatory and inhibitory population of neurons, and the firing rate of these PS is under circadian control. This allows the modeling of the observed temporal dynamics of PS within the framework of the Wilson-Cowan model, under the two conditions of control and epileptogenic state of the brain, in order to elucidate the circadian influence on the pathophysiology of an evolving brain disease.

In accordance with the invention, external modulation of fEPSPs and fIPSPs are used to develop close-loop seizure prevention strategies during the latency period. Specifically, chemical, thermal, and or electrical manipulation of fEPSPs and or fIPSPs (field potentials) in the brain may be carried out in response to a detection of one or more biomarkers in accordance with the invention, whereby seizure is prevented. It should be understood that the invention may be used in connection with any currently known means of manipulating fEPSPs and fIPSPs, as well as manipulation means which are as yet unknown.

Although a close-loop seizure prevention strategy is likely to offer greater efficiency, the invention may be used in connection with non-feedback, or open loop methods, as well as passive controls.

Manipulation of field potentials is targeting to changing, at least, the timing, amplitude, and rate of field potential activity. The target is a restoration of any or all of the normal circadian rhythm, in-phase relationship, and amplitude balance between the fIPSP and fEPSP field potentials.

In accordance with a further embodiment of the invention, a sensor is positioned on or in the head of a patient to be treated. That sensor is then connected to means for producing a change in neuronal activity. Examples of sensors and feedback mechanisms may be found in U.S. Pat. No. 4,735,208 to Wyler, et al.; U.S. Pat. No. 6,529,774 to Green; and U.S. Pat. No. 7,120,486 to Leuthardt, et al.; U.S. Pat. No. 6,978,183 to Rothman; U.S. Pat. No. 7,209,787 to DiLorenzo; and U.S. Patent Publication 2005/0283203 to Flaherty, et al.; 2005/0131311 to Leuthardt, et al.; 2005/0273890 to Flaherty, et al.; 2005/0203366 to Donoghue, et al.; 2006/0058627 to Flaherty, et al.; 2005/0021103 to DiLorenzo; and 2007/0046486 to Donoghue, et al.; and 2005/0240242 to DiLorenzo, all of which are hereby incorporated by reference herein.

In accordance with the invention, it is advantageous to have the sensor or sensor array positioned in the body, whereby a feedback mechanism enables the administration of a correct therapeutic treatment based on observed results, in a closed loop manner. The sensor array may be positioned under the scalp, or within the skull, whereby the latter may enable a smaller sensor, or more reliable measurement, depending upon the sensor type. Of course, sensors may be placed outside of the body, however monitoring may take place over an extended time period, whereupon the presence of external sensors would be deemed disadvantageous or inconvenient.

In a further embodiment, sensors monitor for biomarkers in accordance with the invention. One or more microprocessors may be connected to the sensor output, whereby drift, amplitude and phase measurements may be analyzed and compared with stored normal values, or observed non-latent values for the patient. Upon a match with one or more of the biomarkers, one or more of the following may be carried out: alerting of the patient or health care practitioner through electronic communications; alerting of the patient through mechanical means; administration of temperature change to a determined location in the brain; administration of a chemical systemically; administration of a chemical within the blood brain barrier; administration of a chemical adjacent to a determined location in the brain; and administration of an electrical signal to a determined location in the brain.

The invention provides a method of detecting epileptogenesis in an animal, including these steps: monitoring a firing rate of first population spikes, within the hippocampus of the animal, the first population spikes having a large negative excursion in the measured electrical activity; monitoring a second firing rate of second population spikes, within the hippocampus of the animal, the second population spikes having a large positive excursion in the measured electrical activity; observing, of the monitored firing rates, an increase in the firing rate of the first population spikes, and a concurrent decrease in the firing rate of the second population spikes; wherein the increase and concurrent decrease are indicative of epileptogenesis.

In one embodiment, an indicator of eleptogenesis is an increase in the firing rate of the first population spikes that is sustained over time. Another indicator is where the increase and concurrent decrease represent a phase shift relative to a circadian rhythm. In healthy animals, the firing of the first population spikes and the firing of the second population spikes are observed to be in-phase. Additionally, the increase and concurrent decrease have been observed to occur within one day of an epilepticus inducing event.

In accordance with the invention, the firing rates are observed to have a duration of about 100 to 200 milliseconds. The firing rates are monitored within the CA1 area of the hippocampus. The population spikes are the macroscopic physiological features representing the integrated synaptic activity in the extracellular space generated by synchronous firing of populations of neurons in the brain. The firing rates are the number of spontaneous population spike events observed per unit of time. The invention advantageously observes the firing rates following a status epilepticus inducing brain injury. Epileptogenesis is observed where increase and concurrent decrease represent a change in phase of $3\pi/4$.

In accordance with another aspect of the invention, changes in the circadian rhythm of the core body temperature (CBT) of a patient are associated with epileptogenesis. A study was conducted by the inventors, in which Male Sprague-Dawley rats (n=2) weighing about 265 grams were implanted with a radio frequency transponder in the abdominal cavity and a stimulating electrode in the ventral hippocampus. Following recovery the rats were transferred to a controlled lighting environment of mixed light and dark in a 24 hour period (24 h LD environment), during which time the CBT was continuously monitored. After baseline recordings, the rats were brain injured through electrical stimulation. The CBT rhythm of rats with injured brains was monitored for 4 weeks in a 24 h LD cycle. During this time period, the rats exhibited spontaneous seizures. The rats were then moved to a 24 DD, constant darkness routine environment, and monitored for four additional weeks. The Lomb Scargle periodogram was then used to estimate the period of statistically significant oscillations in the circadian range.

Following injury, after a transient period of 4-5 days, the mean CBT was observed to rise by 0.23+/−0.07 degrees Celcius, and the period of circadian rhythm decreased by 0.3+/−0.01 hours. The phase of CBT oscillation was observed to shift by −1.38+/−0.003 hours.

After the rats were transferred to the 24 DD routine, the mean CBT returned to baseline; however the CBT was not entrained with external light stimuli, and it exhibited an endogenous rhythm with a period of 24.46+/−0.007 hours. The phase was observed to be shifted to 0.95+/−0.6 hours. In addition, a statistically significant peak (p<0.05), at about 12 hours, was observed in the Lomb Scargle periodogram. Any occurrence of spontaneous seizures did not have any observable effect on the rhythm of CBT; however, the statistically significant change in CBT was thus usable as a marker for predicting a future seizure.

Further in light of the foregoing, brain injury transiently disturbs the circadian rhythm of CBT and the rhythm appears to be desynchronized from the LD cycle with a period that is less than the imposed 24 hour period. In addition, a statistically significant peak in CBT rhythm at about 12 hours was observed in epileptic rats under a constant routine protocol. In accordance with the invention, a harmonic in the periodogram of CBT rhythm of about 12 hours, which is unmasked in the constant routine protocol, is induced by seizures. This harmonic in turn shifts the phase of the CBT rhythm, and in turn is, in accordance with the invention, associated with a hyperexcitability observed in an epileptic brain. Data from the aforedescribed study is presented in Table 1.

TABLE 1

Core Body Temperature and Circadian Phase Change

| mean (std) | CBT(Degrees C.) | Period (h) | Phase (rad) |
|---|---|---|---|
| Pre-Stim (L/D) | 37.22 (.1) | 23.77 (.01) | 2.97 (.17) |
| Post-Stim (L/D) | 37.42 (.17)* | 23.66 (.007) | 2.61 (.17)* |
| Post-Stim (D/D) | 37.32 (.2) | 24.47 (.006) | 3.21 (.00)* |
| | | 12.27 (.001)* | |

*Statistically significant difference from baseline (Prestim L/D)

While the invention detects epileptogenesis, the invention further provides means of alerting the patient or others of the impending epileptic event, in one embodiment, by emitting a signal based on the observed increase and concurrent decrease. Once one or more marker events are detected or observed, a signal is emitted from the patient, by a by a device located within or upon the patient.

The invention further provides a system 300 for indicating an impending seizure in a patient 302, where system 300 comprises one or more electrodes 304 positioned proximate the hippocampus 306 of the patient, operable to receive electrical signals from hippocampus 306. Electrode 304 is contemplated to include any type of receiver operative to isolate the faint electrical signals of the hippocampus 306 or brain and transmit them to associated equipment. In addition to the one or more electrodes 304, the invention includes means 308 associated with the electrodes, operative to monitor at least one neuronal field potential in the brain of the patient, including monitoring at least one changed field potential characteristic. These means 308 include electronic or computer based means, or any other means which may be known or hereafter developed which are capable of this function. Any one or more of the following would be monitored: an increase in the frequency of excitatory spikes; a decrease in the frequency of inhibitory spikes; an increase in the frequency of excitatory spikes during a decrease in the frequency of inhibitory spikes; a phase drift of the frequency of excitatory spikes with respect to a circadian rhythm; a phase drift of the frequency of inhibitory spikes with respect to a circadian rhythm; a faster phase drift of the frequency of excitatory spikes than the phase drift of the frequency of inhibitory spikes; a substantially out of phase relationship between excitatory spikes and inhibitory spikes; and a substantially anti-phase relationship between excitatory spikes and inhibitory spikes. Further, a system of the invention includes means 312 for communicating any of said changed field potential characteristics to the patient or others, whereby epileptogenesis is indicated. Communicating means could include a visible light, audio signal, wave transmission, or other known means 314 of signaling or communication.

Alternatively, a system 300' in accordance with the invention for indicating epileptogenesis in an animal, comprises one or more electrodes 304 positioned proximate the hippocampus 306 of the patient 302, operable to receive electrical signals in the form of population spikes, from the hippocampus 306. Further, means 308' are included for monitoring a firing rate of first population spikes, within the hippocampus 306 of the patient 302 or animal, the first population spikes having a large negative excursion in the measured electrical activity. Additionally, means 308' are included for monitoring a second firing rate of second population spikes, within the hippocampus of the animal, the second population spikes having a large positive excursion in the measured electrical activity. Monitoring means are the same as described above. Further included are means 310 for determining, of the monitored firing rates, an increase in the firing rate of the first population spikes, and a concurrent decrease in the firing rate of the second population spikes. Means 310 for determining include electronic or computer based means, or any other means which may be known or hereafter developed which are capable of this function. Additionally, a system of the invention includes means for communicating 312 a means 314 of signal indicative of a determined increase and concurrent decrease to the patient or others, whereby epileptogenesis is indicated. Means 312 for communicating are as described above.

It should be understood that means 308, 308', 310, and or 312 may contain information processing systems, computers, or computing devices 340. Means 308' illustrates computing devices or components that may be included, however it should be understood that means 308, 310, and or 312 may be similarly configured. A mass storage interface 320 is used to connect mass storage devices, such as data storage device 322, to the information processing system 340. One specific type of data storage device is a computer readable medium such a solid state drive 326 of small form factor, or a drive which records on removable media 328. A main memory 330 may be included. Although software may be concurrently resident in the main memory 330, it is clear that respective software component(s) of the main memory 330 are not required to be completely resident in the main memory 330 at all times or even at the same time.

Although only one CPU 332 is illustrated, multiple CPUs 332 can be used equally effectively. Embodiments of the present invention further incorporate interfaces that each includes separate, fully programmed microprocessors that are used to off-load processing from the CPU 332. Terminal interface 334 is used to directly connect one or more terminals 336 to computer 340 to provide a user interface to the computer 340. These terminals 336, which are able to be nonintelligent or fully programmable workstations, are used to allow system administrators and users to communicate with the computing devices 340. The terminal 336 is also able to consist of user interface and peripheral devices that are connected to computer 340 and controlled by terminal interface hardware included in the terminal I/F 334 that includes video adapters and interfaces for keyboards, pointing devices, and the like.

An operating system (not shown) included in the main memory is a suitable multitasking operating system such as the Linux, UNIX, Windows, operating system. Embodiments of the present invention are able to use any other suitable operating system. Some embodiments of the present invention utilize architectures, such as an object oriented framework mechanism, that allows instructions of the components of operating system (not shown) to be executed on any processor located within the information processing system 340. The network adapter hardware 342 is used to provide an interface to the network 344. Embodiments of the present invention are able to be adapted to work with any data communications connections including present day analog and/or digital techniques or via a future networking mechanism. Suitably small and lightweight components are employed for the comfort and convenience of the patient.

Although the exemplary embodiments of the present invention are described in the context of a fully functional computer system, those skilled in the art will appreciate that software embodiments are capable of being distributed as a program product via CD or DVD, e.g. CD 1718, CD ROM, or other form of recordable media, or via any type of electronic transmission mechanism.

Figure 17:
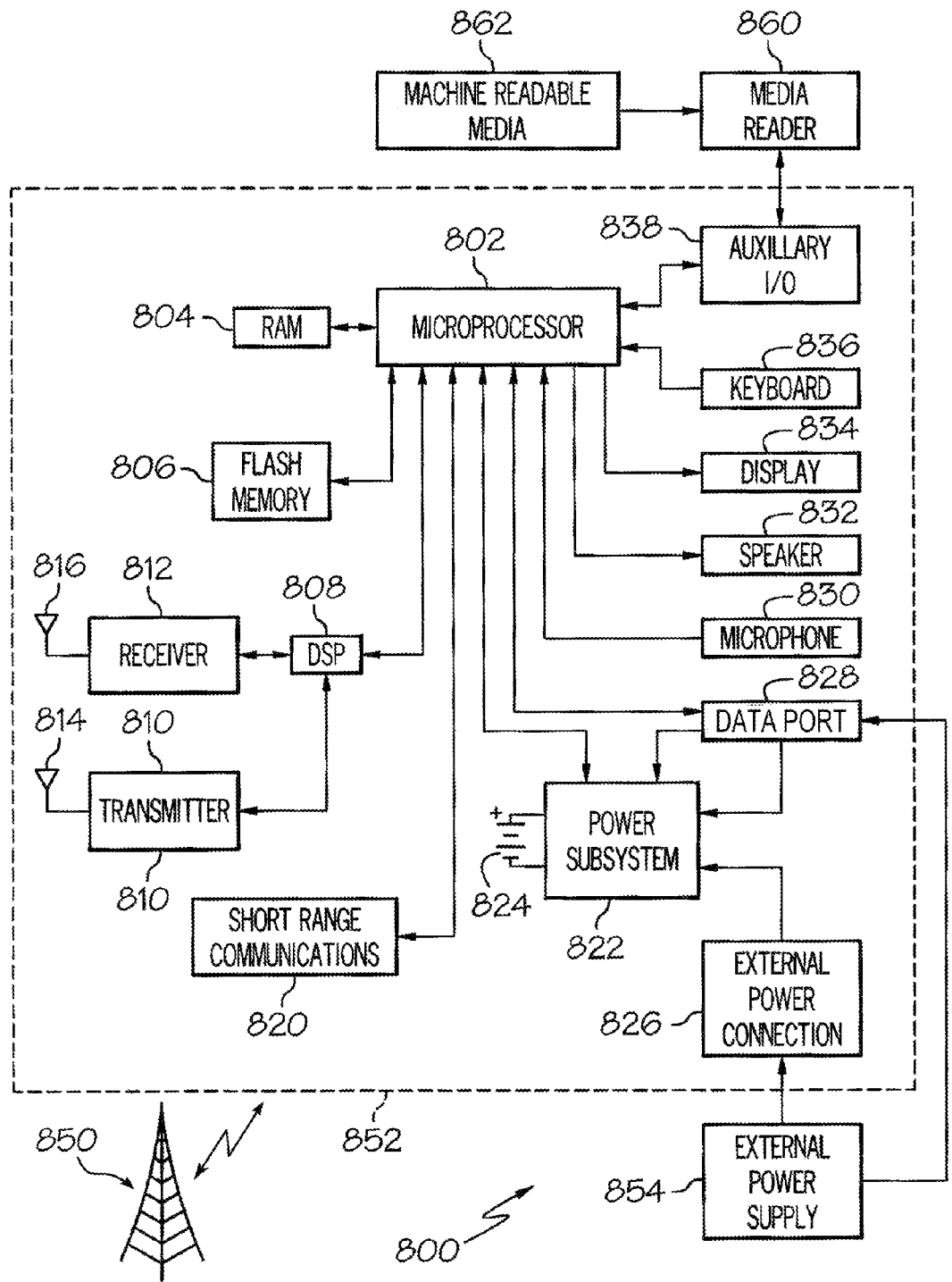
FIG. 17 is a block diagram illustrating a detailed view of an information processing system according to one embodiment of the present invention.

FIG. 17 is a block diagram of an electronic device and associated components 800 in which the systems and methods disclosed herein may be implemented. For example, a device including some or all of the components illustrated in FIG. 17 may be connected to electrodes in accordance with the invention, and may remain with a patient, internal or external to the body, for monitoring. Additionally, a device including some or all of the components of FIG. 17 may be used to analyze recorded data, as described herein. In this example, an electronic device 852 is a wireless two-way communication device with voice and data communication capabilities. Such electronic devices communicate with a wireless voice or data network 850 using a suitable wireless communications protocol. Wireless voice communications are performed using either an analog or digital wireless communication channel. Data communications allow the electronic device 852 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated electronic device 852 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate.

The electronic device 852 includes a microprocessor 802 that controls the overall operation of the electronic device 852. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

A battery 824 is connected to a power subsystem 822 to provide power to the circuits of the electronic device 852. The power subsystem 822 includes power distribution circuitry for providing power to the electronic device 852 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the electronic device 852.

The data port 828 of one example is a receptacle connector 104 or a connector that to which an electrical and optical data communications circuit connector 800 engages and mates, as described above. The data port 828 is able to support data communications between the electronic device 852 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the device by enabling information or software exchange through direct connections between the electronic device 852 and external data sources rather then via a wireless data communication network. In addition to data communication, the data port 828 provides power to the power subsystem 822 to charge the battery 824 or to supply power to the electronic circuits, such as microprocessor 802, of the electronic device 852.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the electronic device 852. A predetermined set of applications that control basic device operations, including at least data and voice communication applications, is able to be installed on the electronic device 852 during manufacture. Examples of applications that are able to be loaded onto the device may be a personal information manager (PIM) application having the ability to organize and manage data items relating to the device user, such as, but not limited to, e-mail, calendar events, voice mails, appointments, and task items.

Further applications may also be loaded onto the electronic device 852 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the electronic device 852 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the electronic device 852 is substantially similar, except that received signals are generally provided to a speaker 832 and signals for transmission are generally produced by a microphone 830. Alternative voice or audio I/O subsystems, such as a voice message recording subsystem, may also be implemented on the electronic device 852. Although voice or audio signal output is generally accomplished primarily through the speaker 832, the display 834 may also be used to provide an indication of the identity of a calling party, the duration of a voice call, or other voice call related information, for example.

Depending on conditions or statuses of the electronic device 852, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the electronic device 852 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above.

A media reader 860 is able to be connected to an auxiliary I/O device 838 to allow, for example, loading computer readable program code of a computer program product into the electronic device 852 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the electronic device through the Data port 828 or computer readable program code is alternatively able to be provided to the electronic device 852 through the wireless network 850.

Methods of detection and control, in accordance with the invention, further include at least the following:

1.0 General modulation (feedback, nonfeedback, passive controls to effect changes in timing, amplitude, rate, . . . ) of parameters or events that mediate excitation in the brain.

1.1 Electrically modulate parameters or events that mediate excitation in the brain 1.2 Chemically modulate parameters or events that mediate excitation in the brain.

1.3 Thermally modulate parameters or events that mediate excitation in the brain.

1.4 Electrically modulate fEPSPs in the brain.

1.5 Chemically modulate fEPSPs in the brain.

1.6 Thermally modulate fEPSPs in the brain.

2.0 General modulation of or events that mediate inhibition in the brain.

2.1 Electrically modulate parameters or events that mediate excitation in the brain 2.2 Chemically modulate parameters or events that mediate excitation in the brain.

2.3 Thermally modulate parameters or events that mediate excitation in the brain.

2.4 Electrically modulate fIPSPs in the brain.

2.5 Chemically modulate fIPSPs in the brain.

2.6 Thermally modulate fIPSPs in the brain.

3.0 General modulation of or events that mediate the balance between inhibition and excitation in the brain.

3.1 Electrically modulate parameters or events that mediate the balance between excitation and inhibition in the brain.

3.2 Chemically modulate parameters or events that mediate the balance between excitation and inhibition in the brain.

3.3 Thermally modulate parameters or events that mediate the balance between excitation and inhibition in the brain.

3.4 Electrically modulate the balance between fEPSPs and fIPSPs in the brain.

3.5 Chemically modulate fEPSPs and fIPSPs in the brain.

3.6 Thermally modulate fEPSPs and fIPSPs in the brain.

4.0 Modulate the observed circadian rhythm as in items 1.0, 2.0, and 3.0, above.

5.0 A closed-loop neural modulation system of items 1-3 for use in treating disease which provides general modulation and which may be varied, comprising a neuromodulation and recording unit, said neuromodulation and recording unit further comprising a reference module in communication with a patient interface module, a supervisory module, and a control circuit, said reference module further comprising a memory register for the storage of control law reference values, said control law employing nonlinear control, and said supervisory module facilitating monitoring and adjustment of reference values by a health care provider.

6.0 A method for determining patient-specific, optimal neuromodulation parameters of items 1-3 of a neuromodulation signal for controlling seizures in a patient with epilepsy the method comprising: analyzing an fEPSPs and fIPSPs from a patient to detect and/or predict seizure activity; delivering a neuromodulation of items 1-3 to the patient with an implanted device and recording unit when the analysis of the brain signal detects and/or predicts seizure activity, wherein the neuromodulation stimulus comprises a set of neruomodulation parameters; recording the patient's response to the neuromodulation; real-time automatic determination of parameters for a ongoing neuromodulation, wherein the neuromodulation modality of items 1-3 comprises at least one changed parameter from the set of predetermined neuromodulation parameters; wirelessly transmitting data that is indicative of the patient's response to neuromodulation, and programming the implanted neuromodulation and recording unit with the determined substantially optimal stimulation parameters.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

The following references are incorporated by reference herein, in their entirety:

[1] P. Andersen, T. V. P. Bliss, K. K. Skrede, Lamellar organization of hippocampal excitatory pathways, Exp. Brain Res. 13 (1971) 222-238.

[2] C. A. Barnes, B. L. McNaughton, G. V. Goddard, R. M. Douglas, R. Adamec, Circadian rhythm of synaptic excitability in rat and monkey central nervous system, Science 197 (1977) 91-92.

[3] A. Bragin, G. Jando, Z. Nadasdy, M. van Landghem, G. Buzsaki, Dentate eeg spikes and associated interneuronal population bursts in the hippocampal hilar region of the rat, J. Neurophysiol. 73 (4) (1995) 1691-1705.

[4] R. P. Brenner, Eeg in convulsive and nonconvulsive status epilepticus, J. Clin. Neurophysiol. 21 (2004) 319-331.

[5] G. Buzsaki, Hippocampal sharp waves: their origin and significance, Brain Res. 398 (1986) 242-252.

[6] D. Chaudhary, L. M. Wang, C. S. Colwell, Circadian regulation of hippocampal long term potentiation, J. Biol. Rhythms 20 (2005) 225-236.

[7] H. Cline, Synaptogenesis: a balancing act between excitation and inhibition, Curr. Biol. 15 (2005) R203-R205.

[8] R. Cossart, C. Dinocourt, J. C. Hirsch, A. Merchan-Perez, J. De Felipe, Y. Ben Ari, C. Esclapez, M. Bernard, Dendritic but not somatic gabaergic inhibition is decreased in experimental epilepsy, Nat. Neurosci. 4 (2001) 52-62.

[9] G. W. Davis, Homeostatic control of neural activity: from phenomenology to molecular design, Ann. Rev. Neurosci. 29 (2006) 307-323.

[10] F. Du, R. Schwarcz, Amino-oxyacetic acid causes selective neuronal loss in layer iii of the rat medial entorhinal cortex, Neurosci. Lett. 147 (1992) 185-188.

[11] L. El-Hassar, M. Milh, F. Wendling, N. Ferrand, M. Esclapez, C. Bernard, Cell domain-dependent changes in the glutamatergic and gabaergic drives during epileptogenesis in the rat ca1 region, J. Physiol. 578 (2007) 193-211.

[12] M. S. Fee, P. P. Mitra, D. Kleinfeld, Automatic sorting of multiple unit neuronal signals in the presence of anisotropic and non-Gaussian variability, J. Neurosci. Methods 69 (1996) 175-188.

[13] W. B. Knowles, P. A. Schwartzkroin, Local circuit synaptic interactions in hippocampal brain slices, J. Neurosci. 1 (1981) 318-322.

[14] J. C. Lacaille, P. A. Schwartzkroin, Stratum lacunosum-moleculare interneurons of hippocampal ca1 region. ii. Intras-matic and intradendritic recordings of local circuit interactions, J. Neurosci. 8 (1988) 1411-1424.

[15] R. R. Llinas, U. Ribary, D. Jeanmonod, E. Kronberg, P. P. Mitra, Thalamocortical dysrthythmia: a neurological and neuropsychiatric syndrome characterized by magnetoencephalography, Proc. Natl. Acad. Sci. 96 (1999) 15222-15227.

[16] E. W. Lothman, E. H. Bertram, J. W. Bekenstein, J. B. Perlin, Self sustaining limbic status epilepticus induced by continuous hippocampal stimulation; electrographic and behavioral characteristics, Epilepsy Res. 3 (1989) 107-119.

[17] L. H. A. Monteiro, M. A. Bussab, B. J. G. Chaui, Analytical results on Wilson-Cowan neuronal network modified model, J. Theor. Biol. 219 (2002) 83-91.

[18] J. L. Rubenstein, M. M. Merzenich, Model of autism: increased ratio of excitation/inhibition in key neural systems, Genes Brain Behav. 2 (2003) 255-267.

[19] J. C. Sanchez, T. M. Mareci, W. Norman, J. Principe, W. L. Ditto, P. R. Carney, Evolving into epilepsy: multiscale electrophysiological analysis and imaging in an animal model, Exp. Neurol. 198 (2006) 31-47.

[20] H. S. Singer, K. Minzer, Neurobiology of tourette's syndrome: concepts of neuroanatomic localization and neurochemical abnormalities, Brain Dev. 25 (2003) S70-S84.

[21] S. S. Talathi, D. U. Hwang, M. L. Spano, J. Simonotto, M. D. Furman, S. M. Myers, J. T. Winters, W. L. Ditto, P. R. Carney, Non-parametric early seizure detection in an animal model of temporal lobe epilepsy, J. Neural. Eng. 5 (2008) 85-98.

[22] A. Wassef, J. Baker, L. D. Kochan, Gaba and schizophrenia: a review of basic science and clinical studies, J. Clin. Psychopharmacol. 23 (2003) 601-640.

[23] H. R. Wilson, J. D. Cowan, Excitatory and inhibitory interactions in localized populations of model neurons, Biophys. J. 12 (1972) 1-24.

[24] Sander, J. W. & Shorvon, S. D. Epidemiology of the epilepcies. J Neurol Neurosurg Psychiatry. 61, 433-443 (1996).

[25] King, D. & Spencer, S. Invasive electroencephalography in mesial temporal lobe epilepsy. J Clin Neurophysiol. 12, 32-45 (1995).

[26] De Curtis, M. & Avanzini, G. Interictal spikes in focal epileptogenesis. Prog Neuobiol. 63, 541-567 (2001).

[27] Huifang, L. & Prince, D. A. Synaptic Activity in Chronically Injured, Epileptogenic Sensory-Motor Neocortex. J Neurophysiol. 88, 2-12, (2002).

[28] Dudek, F. E. & Staley, K. J. How Does the Balance of Excitation and Inhibition Shift during Epileptogenesis? Epilepsy Curr. 7, 86-88 (2007)

[29] Shao, L. R. & Dudek F. E. Increased Excitatory Synaptic Activity and Local Connectivity of Hippocampal CA1 Pyramidal Cells in Rats With Kainate-Induced Epilepsy. J Neurophysiol 92, 1366-1373, (2004)

[30] Lorente de No, R. Action potential of the motoneurons of the hypoglossus nucleus. J Cell Comp Physiol. 29, 207-287 (1947).

[31] King, C., Henze, D. A., Leinekugel, X., Buszaki, G. Hebbian modification of a hippocampal population pattern in the rat. J Physiol. 521, 159-167 (1999)

[32] Csicsvari, J., Hirase, H., Czurko, A., Buzsaki, G. Reliability and state dependence of pyramidal cell-interneuron synapses in the hippocampus: an ensemble approach in behaving rat. Neuron. 21, 179-189 (1998)

[33] Smith, B. N. & Dudek, F. E. Short- and Long-Term Changes in CA1 Network Excitability After Kainate Treatment in Rats. J Neurophysiol. 85, 1-9 (2001)

[34] Quigg, M. Circadian rhyths: interactions with seizures and epilepsy. Epilepsy Res. 42, 43-55 (2000)

[35] Quigg, M., Straume, M., Menaker, M., Bertram, E. Effects of circadian regulation of rest-activity state on spontaneous seizures in a rat model of limbic epilepsy. Epilepsia. 41, 502-509 (2000)

[36] Quigg, M., Straume, M., Smith, T., Menaker M., Bertram, E. Seizures induce phase shifts of rat circadian rhythm. Brain Res. 913, 165-169 (2001)

What is claimed is:

1. A method of detecting an impending seizure in a patient, the method comprising the steps of:
   monitoring at least one neuronal field potential in the brain of the patient,
   including monitoring at least one changed field potential characteristic selected from the group consisting of:
   an increase in the frequency of excitatory spikes during a decrease in the frequency of inhibitory spikes,
   a phase drift of the frequency of excitatory spikes with respect to a circadian rhythm,
   a phase drift of the frequency of inhibitory spikes with respect to a circadian rhythm,
   a faster phase drift of the frequency of excitatory spikes than the phase drift of the frequency of inhibitory spikes,
   a substantially out of phase relationship between excitatory spikes and inhibitory spikes, and
   a substantially anti-phase relationship between excitatory spikes and inhibitory spikes;
   wherein any of said changed field potential characteristics is indicative of epileptogenesis; and
   carrying out a therapeutic response if epileptogenesis is indicated, the response operative to reduce the likelihood of a seizure.

2. The method of claim 1, further comprising:
   producing a response operative to reduce the likelihood of a seizure, based on a monitored change in the at least one selected field potential characteristic, said response selected from the group consisting of:
   changing a temperature in the brain; releasing a chemical in the body; and administering an electrical impulse within the body.

3. The method of claim 2, wherein said produced response is changed over time, in response to further monitoring, in a closed-loop process.

4. A method of detecting epileptogenesis in a patient, comprising the steps of:
   monitoring an fEPSP and an fIPSP of the hippocampus of the patient over time, to detect at least one change selected from the group consisting of:
   an increase in the frequency of fEPSP discharges during a decrease in the frequency of fIPSP discharges,
   a phase drift of the frequency of fEPSP discharges with respect to a circadian rhythm,
   a phase drift of the frequency of fIPSP discharges with respect to a circadian rhythm,
   a faster phase drift of the frequency of fEPSP discharges than the phase drift of the frequency of fIPSP discharges,
   a substantially out of phase relationship between fEPSP discharges and fIPSP discharges, and
   a substantially anti-phase relationship between fEPSP discharges and fIPSP discharges;
   wherein each of said monitored changes is further indicative of epileptogenesis, whereupon therapeutically beneficial measures are taken on behalf of the patient selected from the group consisting of changing a temperature in the brain, releasing a chemical in the body, and administering an electrical impulse within the body.

5. The method of claim 4, wherein a further beneficial measure is selected from the group consisting of:
   notifying the patient;
   notifying a health care practitioner; and
   administering a therapeutic remedy operative to reduce the likelihood of a seizure.

6. A method of detecting an impending seizure in a patient, and treating the patient, the method including the steps of:
   monitoring at least one neuronal field potential in the brain of the patient, including monitoring at least one changed field potential characteristic selected from the group consisting of:
   an increase in the frequency of excitatory spikes combined with a decrease in the frequency of inhibitory spikes,
   an increase in the frequency of excitatory spikes during a decrease in the frequency of inhibitory spikes,
   a phase drift of the frequency of excitatory spikes with respect to a circadian rhythm, and
   a phase drift of the frequency of inhibitory spikes with respect to a circadian rhythm;
   emitting a signal, based on a monitored change in the at least one selected field potential characteristic, said response selected from the group consisting of:
   transmitting an electrical signal outside the body; producing a result in the body detectible by the patient; transmitting an electrical signal from the body to a wireless network; transmitting an electrical signal from the body to an electronic receiver;
   whereby the emitted signal is operative to initiate events operative to reduce the likelihood of a seizure.

7. The method of claim 6, wherein said group of at least one changed field potential characteristic further includes:
   a faster phase drift of the frequency of excitatory spikes than the phase drift of the frequency of inhibitory spikes;
   a substantially out of phase relationship between excitatory spikes and inhibitory spikes; and
   a substantially anti-phase relationship between excitatory spikes and inhibitory spikes.

8. A method of treating epileptogenesis in an animal, comprising:
   monitoring a firing rate of first population spikes within the hippocampus of the animal;
   monitoring a second firing rate of second population spikes within the hippocampus of the animal;
   observing, of the monitored firing rates, a phase drift of the frequency of excitatory spikes with respect to a circadian rhythm, and a phase drift of the frequency of inhibitory spikes with respect to a circadian rhythm, wherein said phase drift is indicative of epileptogenesis; and
   carrying out a therapeutic response if epileptogenesis is indicated, the response operative to reduce the likelihood of a seizure.

9. The method of claim 8, wherein the increase in the firing rate of the first population spikes is sustained over time.

10. The method of claim 8, wherein said increase and concurrent decrease represent a phase shift relative to a circadian rhythm.

11. The method of claim 8, wherein in the observing step, the firing of the first population spikes and the firing of the second population spikes are observed to be in-phase in healthy animals.

12. The method of claim 8, wherein said increase and concurrent decrease occur within one day of an epilepticus inducing event.

13. The method of claim 8, wherein said firing rates have a duration of about 100 to 200 milliseconds.

14. The method of claim 8, wherein said firing rates are monitored within the CA1 area of the hippocampus.

15. The method of claim 8, wherein said population spikes are the macroscopic physiological features representing the integrated synaptic activity in the extracellular space generated by synchronous firing of populations of neurons in the brain.

16. The method of claim 8, wherein said firing rates are the number of spontaneous population spike events observed per unit of time.

17. The method of claim 8, wherein said firing rates are observed following a status epilepticus inducing brain injury.

18. The method of claim 8, wherein said increase and concurrent decrease represent a change in phase of $3\pi/4$.

19. The method of claim 8, further including:
emitting a signal based on said observed increase and concurrent decrease, said signal operative to provide an alert.

20. The method of claim 19, wherein said signal is emitted by a device located within or upon the patient.

21. A system for indicating an impending seizure in a patient, the system comprising:
one or more electrodes positioned proximate the hippocampus of the patient, operable to receive electrical signals from the hippocampus;
means associated with said one or more electrode, operative to monitor at least one neuronal field potential in the brain of the patient, including monitoring at least one changed field potential characteristic selected from the group consisting of:
an increase in the frequency of excitatory spikes during a decrease in the frequency of inhibitory spikes,
a phase drift of the frequency of excitatory spikes with respect to a circadian rhythm,
a phase drift of the frequency of inhibitory spikes with respect to a circadian rhythm,
a faster phase drift of the frequency of excitatory spikes than the phase drift of the frequency of inhibitory spikes,
a substantially out of phase relationship between excitatory spikes and inhibitory spikes, and
a substantially anti-phase relationship between excitatory spikes and inhibitory spikes; and
means for communicating any of said changed field potential characteristics to the patient or others, whereby epileptogenesis is indicated.

22. A system for indicating epileptogenesis in an animal, comprising:
one or more electrodes positioned proximate the hippocampus of the patient, operable to receive electrical signals in the form of population spikes, from the hippocampus;
means for monitoring a firing rate of first population spikes within the hippocampus of the animal;
means for monitoring a second firing rate of second population spikes within the hippocampus of the animal;
means for determining, of the monitored firing rates, a phase drift of the frequency of excitatory spikes with respect to a circadian rhythm, and a phase drift of the frequency of inhibitory spikes with respect to a circadian rhythm;
means for communicating phase drift to the patient or others, whereby epileptogenesis is indicated.

23. The method of claim 1, wherein the group of changed field potential further includes: a change in the circadian rhythm of core body temperature.

24. The method of claim 1, where in one of the at least one changed field potential characteristic monitored includes an increase in the frequency of excitatory spikes combined with a decrease in the frequency of inhibitory spikes.

* * * * *